US006277970B1

(12) United States Patent
Prusiner et al.

(10) Patent No.: US 6,277,970 B1
(45) Date of Patent: Aug. 21, 2001

(54) PRP-LIKE GENE

(75) Inventors: Stanley B. Prusiner; Patrick Tremblay; Richard Moore, all of San Francisco, CA (US); David Westaway, Etobicoke (CA); Leroy E. Hood; Inyoul Lee, both of Seattle, WA (US)

(73) Assignees: The Regents of the University of California, Oakland, CA (US); The University of Washington, Seattle, WA (US); Governing Council of the University of Toronto, Toronto (CA)

( * ) Notice: Subject to any disclaimer, the term of this patent is extended or adjusted under 35 U.S.C. 154(b) by 0 days.

(21) Appl. No.: 09/309,317

(22) Filed: May 11, 1999

(51) Int. Cl.$^7$ .......................... C07H 21/02; C07H 21/04; C12Q 1/68
(52) U.S. Cl. .................... 536/23.1; 536/23.72; 536/23.5; 536/25.3; 435/69.1; 435/252.3; 435/6; 530/350
(58) Field of Search ............................ 435/69.1, 6, 252.3; 530/350; 536/23.1, 23.72, 23.5, 25.3; 800/4, 8, 9, 18

(56) References Cited

FOREIGN PATENT DOCUMENTS

0327390 * 8/1989 (EP) .

OTHER PUBLICATIONS

Lee et al., Genome Research (1998) 8:1022–1037.*
Moore et al., *J. Mol. Biol.*, 292:797–817 (1999).
Alpers, "Epidemiology and Ecology of Kuru," *Slow Transmissible Diseases of the Nervous System*, vol. 1, S.B. Prusiner and W.J. Hadlow, eds. (New York: Academic Press), pp. 66–90 (1979).
Basler et al., "Scrapie and Cellular PrP Isoforms Are Encoded by the Same Chromosomal Gene," *Cell*, (Aug. 1, 1989), 46:417–28.
Billeter, et al., "Prion Protein NMR Structure and Species Barrier for Prion Diseases," *Proc. Natl. Acad. Sci. USA* (Jul. 1997), 94:7281–7285.
Bolton et al., "Identification of a Protein That Purifies with the Scrapie Prion," *Science* (Dec. 24, 1982) 218:1309–11 (1982).
Brown et al., "Friendly Fire" in Medicine: Hormones, Homografts, and Creutzfeldt–Jakob Disease, *Lancet* (Jul. 4, 1992) 340:24–27.
Chazot, et al., "New Variant of Creutzfeldt–Jakob disease in a 2–year–old French Man," *Lancet* (Apr. 27, 1996) 347(9009):1181.
Donne et al., "Structure of the Recombinant Full–Length Hamster Prion Protein PrP (29–231): The N Terminus is Highly Flexible," *Proc. Natl. Acad. Sci. USA* (Dec. 1997) 94:13452–13457.
Gajdusek et al., "Experimental Transmission of a Kuru–Like Syndrome to Chimpanzees," *Nature* (Feb. 19, 1966) 209(5025);794–796.
Gajdusek, "Unconventional Viruses and the Origin and Disappearance of Kuru" *Science* (Sep. 2, 1977), 197(4307):943–960.
Gibbs, Jr., et al., "Creutzfeldt–Jakob Disease (Spongiform Encephalopathy): Transmission to the Chimpanzee," *Science* (Jul. 1968), 161:388–389.
Gibbs, Jr., et al., "Strain Variation in the Viruses of Creutzfeldt–Jakob Disease and Kuru," *Slow Transmissible Diseases of the Nervous System*, vol. 2, S.B. Prusiner and W.J. Hadlow, eds. (New York: Academic Press), pp.87–110 (1979).
Goldfarb et al., Fatal Familial Insomnia and Familial Creutzfeldt–Jakob Disease: Disease Phenotype Determined by a DNA Polymorphism, *Science*, (Oct. 30, 1992) 258:806–808.
Hadlow, "Scrapie and Kuru," *Lancet* (Sep. 5, 1959), 2:289–290.
Harries–Jones et al., "Creutzfeldt–Jakob Disease in England and Wales, 1980–1984: a Case–Control Study of Potential Risk Factors," *J. Neurol. Neurosurg. Psychiatry* (1988) 51:1113–1119.
Hsiao et al., "Inherited Human Prion Diseases," *Neurology* (Dec. 1990), 40:1820–1827.
James et al., "Solution Structure of a 142–Residue Recombinant Prion Protein Corresponding to the Infectious Fragment of the Scrapie Isoform," *Proc. Natl. Acad. Sci. USA* (Sep. 1997), 94:10086–10091.
Kitamoto et al., "Human Prion Diseases With Variant Prin Protein," *Phil. Trans. R. Soc. Lond. B*, (1994) 343:391–398.
Klatzo et al., "Pathology of Kuru," *Laboratory Investigation*, (Jul./Aug. 1959) 8(4):799–847.
McKinley et al., "A Protease–Resistant Protein Is a Structural Component of the Scrapie Prion," *Cell* (Nov. 1983) 35:57–62.
Medori et al., Fatal Familial Insomnia, A Prion Disease With a Mutation at Codon 178 of The Prion Protein Gene, *New England Journal of Medicine*, (Feb. 13, 1992), 326(7):444–449.

(List continued on next page.)

Primary Examiner—Karen Cochrane Carlson
Assistant Examiner—Stephen Tu
(74) Attorney, Agent, or Firm—Dianna L. DeVore; Bozicevic, Field & Francis LLP

(57) ABSTRACT

The present invention provides nucleic acids encoding the Doppel ("Dpl") protein, Dpl peptides, and assays utilizing the Dpl nucleic acids and/or peptides. In related aspects the invention features expression vectors and host cells comprising nucleic acids that encode a human Dpl polypeptide. The present invention also relates to antibodies that bind specifically to a human Dpl polypeptide, methods for producing human Dpl polypeptides, methods for identifying cells expressing Dpl, methods for using the Dpl gene and the Dpl polypeptide to alter cellular function and prion infectivity in culture or in vivo, and identification of individuals at risk for prion disorders by detecting alteration in Dpl coding and regulatory sequences and Dpl expression levels.

9 Claims, 8 Drawing Sheets

OTHER PUBLICATIONS

Figures 1A, 1B:
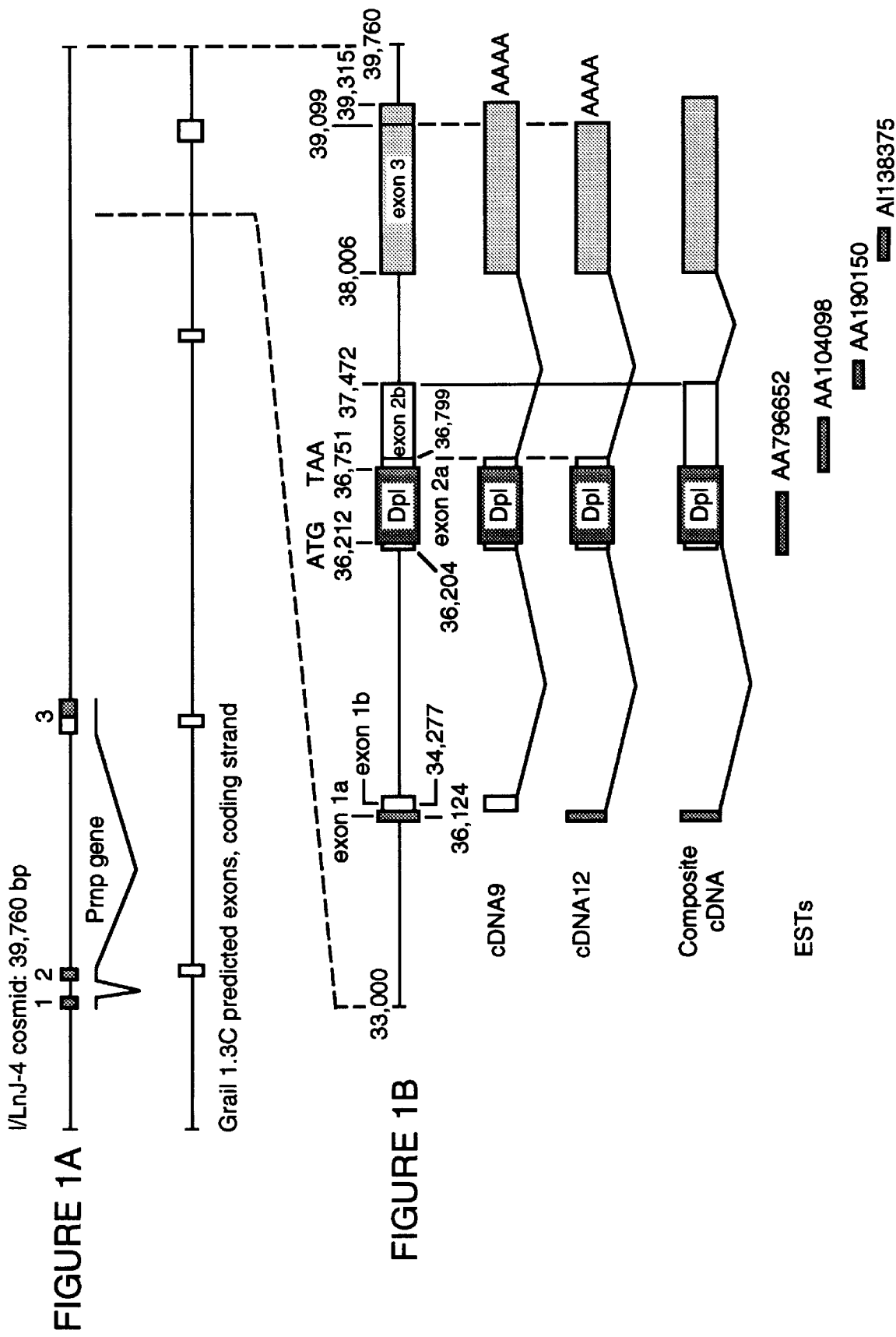

Peretz et al., "A Conformational Transition at the N-terminus of the Prion Protein Features in Formation of the Scrapie Isoform," *Journal of Molecular Biology*, (1997). 273:614–622.

Prusiner et al., "Further Purification and Characterization of Scrapie Prions," *Biochemistry* (1982), 21(26):6942–50.

Prusiner, et al., "Purification and Structural Studies of a Major Scrapie Prion Protein," *Cell* (Aug. 1984), 38:127–134.

Prusiner, "Molecular Biology of Prion Disease," *Science* (Jun. 14, 1991), 252:1515–1522.

Rogers, et al., "Conversion of Truncated and Elongated Prion Proteins into the Scrapie Isoform in Cultured Cells," *Proc. Natl. Acad. Sci. USA* (Apr. 1993), 90:3182–3186.

Tateishi et al., "Prion Protein Gene Analysis and Transmission Studies of Creutzfeldt–Jakob Disease,", *Prion Diseases of Humans and Animals*, Prusiner et al., (London: Ellis Horwood), (1992) pp. 129–134.

Telling, et al., Prion Propagaton in Mice Expressing Human and Chimeric PrP Transgenes Implicates the Interaction of Cellular PrP with Another Protein, *Cell* (Oct. 6, 1995), 83:79–90.

Telling et al., "Evidence for the Conformation of the Pathologic Isoform of the Prion Protein Enciphering and Propagating Prion Diversity," *Science* (Dec. 20, 1996), 274:2079–2082.

Wilesmith, et al., "Bovine Spongiform Encephalopathy," *Current Topics in Microbiology an Immunology*, (1991) 172:21–38.

Will, et al., "A New Variant of Creutzfeldt–Jakob Disease in the UK," *Lancet* (Apr. 6, 1996), 347:921–925.

\* cited by examiner

FIGURE 2A  ctggagctcggtagagaggccccctccccctgcagcgctatatagctgagtgtggccaggcaaggtgTTCCG 34075

GAGAAGTGAGGGCTCCAAGCTTCAGAGCTTCAGAGGCCCACAGTAGCAGAGAACCGAGTATGTGCGGGATTTCCCAGACCA 34150
                         exon 1a---><---exon 1b

AGCAGTGGCTTGTGACTTCCCTTCCAGCCCCTCCCTGTCCCAGGCAGGAGGGATGCTAGGAGCCTGCTC 34225

ATTCATTCCTAGCTGCCTCAGTATTCCTATGCTCTGATGCTCTGGAAATGtaggtactttgggctaactgg 34300
                                          exon 1b---><---intron 1

FIGURE 2B  atctgtcactgttggagggtgggaggcacctgaggagagagtgacagccagcctttccttgcagATTCACC 36211
                                                              intron 1---><---exon 2a ATGAAGAACCTGGAGCTACATGCTGGGTGGCCATCTCCTGCAATGCTGCTTGCCAGCCACCTCCTCCACGTCAAG 36286
MetLysAsnArgLeuGlyThrTrpTrpValAlaIleLeuCysMetLeuLeuAlaSerHisLeuSerThrValLys GCAAGGGGCATAAAGCACAGAGTTCAAGTGGAACCGGAAGTCCTGCCCAGCAGCGGCGGCCAGATCACCGAAGCT 36361
AlaArgGlyIleLysHisArgPheLysTrpAsnArgLysValLeuProSerGlyGlyGlnIleThrGluAla CGGGTAGCTGAGAACCGCCCAGGAGCCTTCATCAAGCAAGGCCGGAAGCTGGACATCGACTTTGGAGCAGAGGC 36436
ArgValAlaGluAsnArgProGlyAlaPheIleLysGlnArgLysLeuAspIleAspPheGlyAlaGluGly AACAGGTACTACGCGGCTAACTATTGCCAGTTCCCTGATGGAATCTACTACGAAGGCTGCTCTGAAGCCAACGTG 36511
AsnArgTyrTyrAlaAlaAsnTyrTrpGlnPheProAspGlyIleTyrTyrGluGlyCysSerGluAlaAsnVal ACCAAGGAGATGCTGGTGACCAGCTGCGTCAACAGCTGCCACCAGGCGGCCAACGCTGAGTTCTCCCGGAGAAG 36586
ThrLysGluMetLeuValThrSerCysValAsnAlaThrGlnAlaAlaAsnGlnAlaGluPheSerArgGluLys CAGGATAGCAAGTCCACCAGCGAGTCCTGTTGGGCGGCTGATCAAAGAGATCTGCTCCGCAAGCACTGCGATTC 36661
GlnAspSerLysLeuHisGlnArgValLeuTrpArgLeuIleLysGluIleCysSerAlaLysHisCysAspPhe TGGCTGGAAAGGGGAGCTGCGCTTCGGGTGCGCGTGACCAACCGCGATGGTCCTGCTCGGGTTTCGTTTGG 36736
TrpLeuGluArgGlyAlaLeuArgValAlaValAspGlnProAlaMetValCysLeuLeuGlyPheValTrp TTCATTGTGAAGTAAAGATCAATGAAGCTGGCAGCCACAGAAGCTGGAGCTGTGGGCAAAGGTAGACAGAGGTAGC 36811
PheIleValLyster          exon 2a---><---exon 2b

FIGURE 2C CTGGTGTTTGCTGGTTGGGCCCCTGCAATGTCTgcaaagttaagaaaaccttttaagtgacacattgtgcgtgc 37515
...exon 2b---><----intron 2...

FIGURE 2D aaatgtttaaaaatctttaagATTCTTCCACAGGTTTCCTCACCTTTCAGGACTCCAGGAGTTGCTGAGCGGG 38035
...intron 2---><----exon 3a...                                                    <----exon 3b

FIGURE 2E TACATTACAACCCTTAAAATACAACGATCACTTGTATAATATATTGTTTCTCTGCGGTTTGTATTCCTGATTTAGT 39135
...exon 3a---><----exon 3c

GGAATGCCATTAAACTCTCTGGGTCAGTATCTCAGTTAACTAGTCCTTTTAGATGACCATGAAGT 39210

ATTCCACAGTACAGATGTGCTGCAAGTGACTTGATAACTTCCTTGTTGACAGATCTTCAGATTGTTCTTATCTTG 39285

CAAACAATAAACACCCATACATATACAGACAgccacggtgtctggtggttttatttctgcagaaaagagtcactg 39360
exon 3c--->

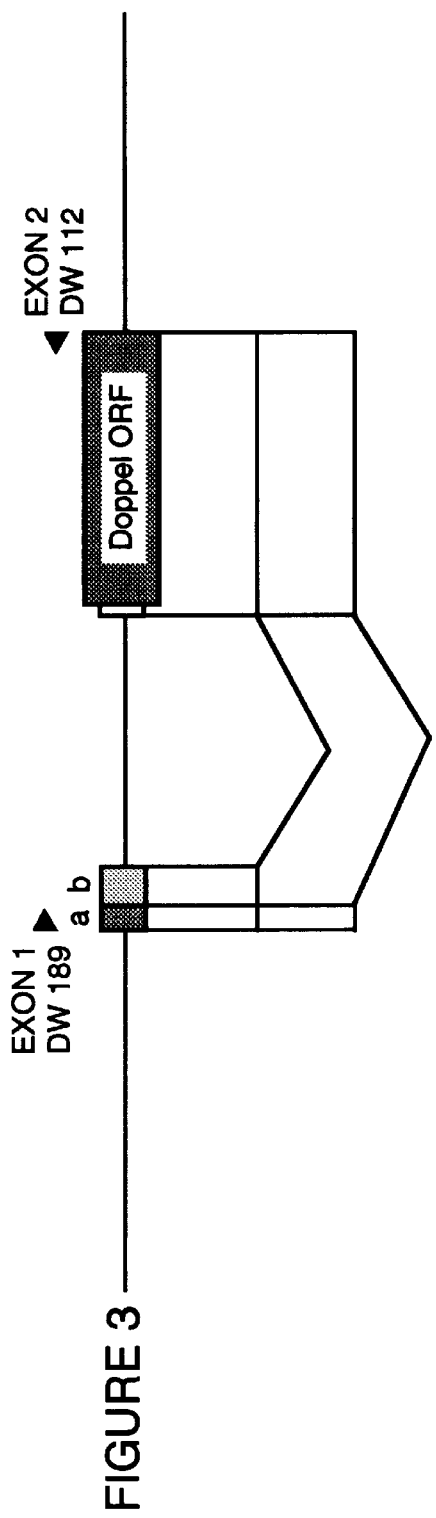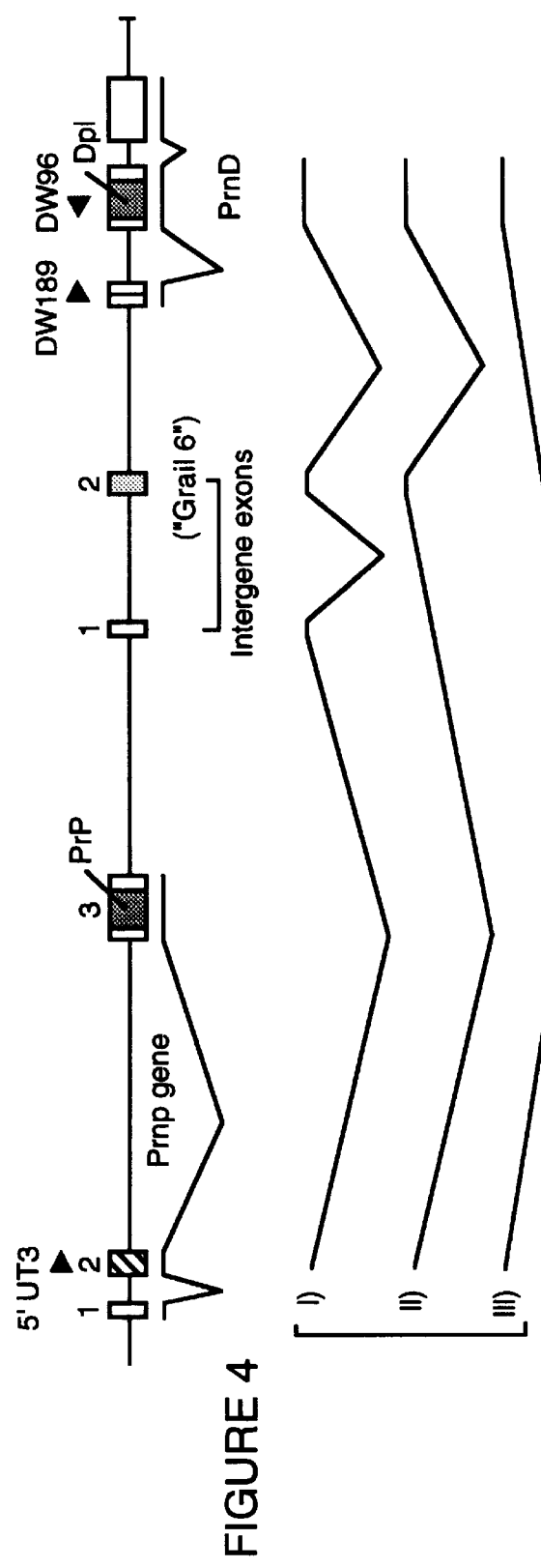
FIGURE 3
FIGURE 4

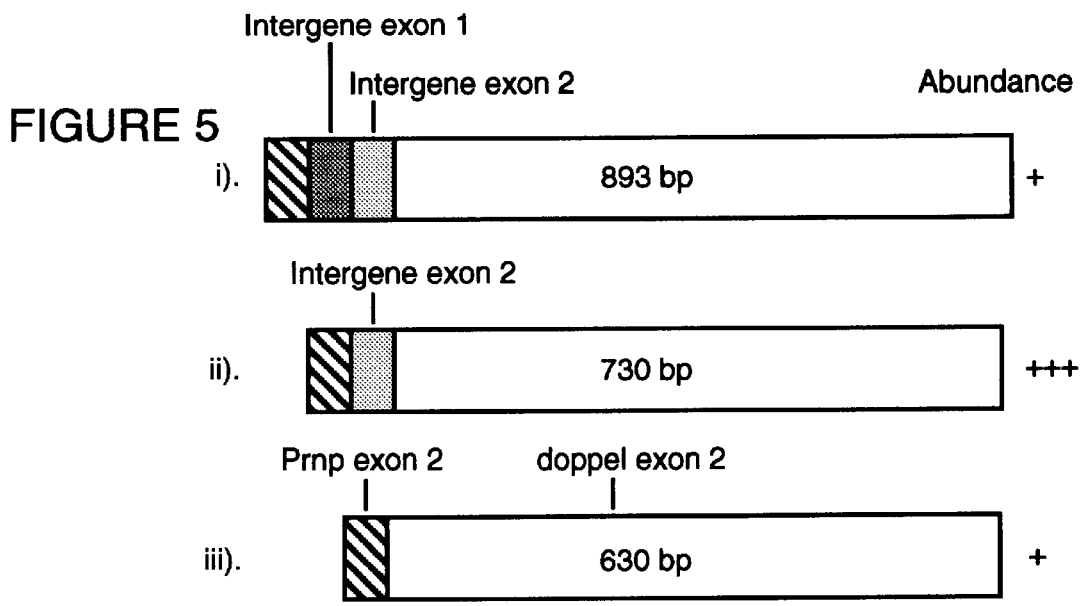
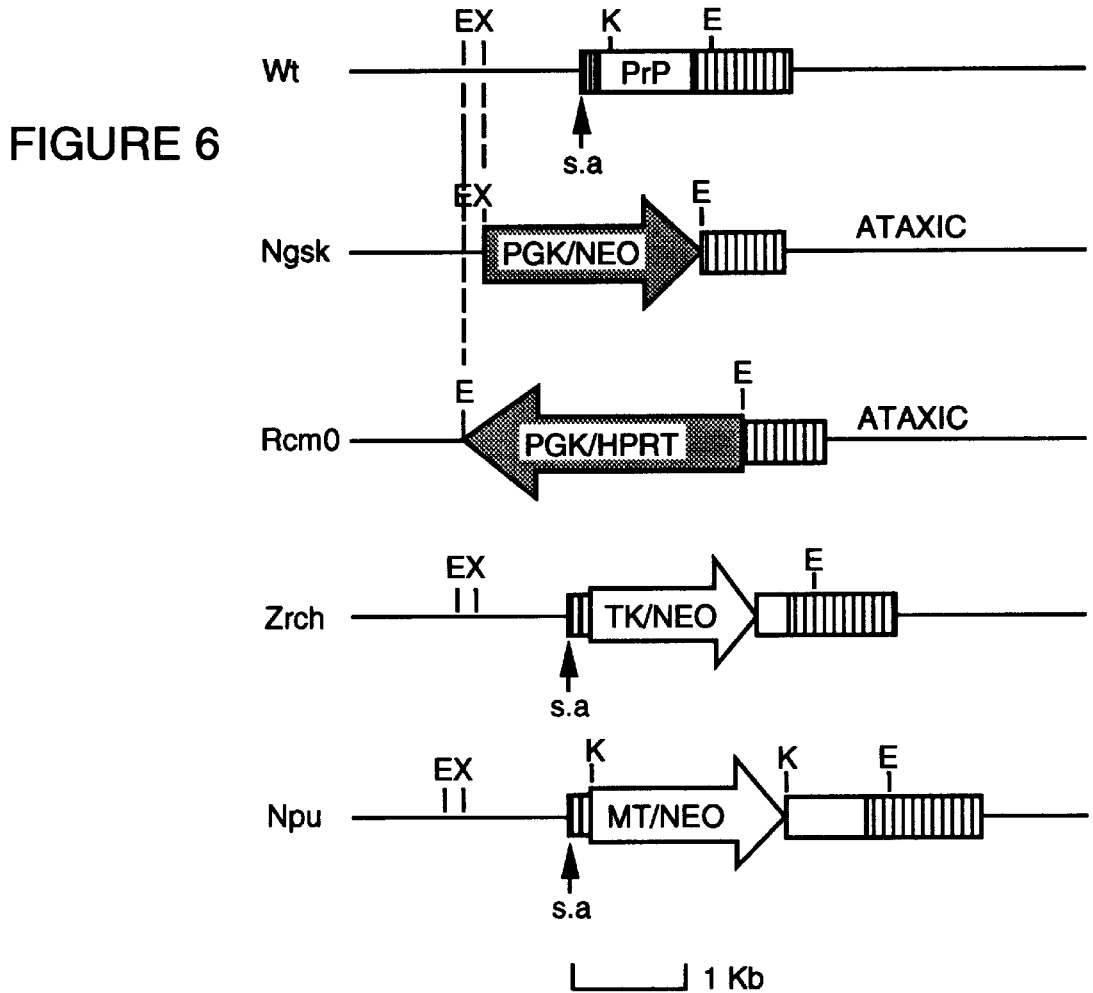

```
human      .........KRkh[LswWWLAtVCMLLfSHLSaVqtRGIKHRtKWNRKaLPSTA.QITEA****..
mouse      MKNRLGTWVAILCMLLASHLSTVKARGIKHRFKWNRKVLPSSGQITEA****..
rat        MKNRLGTWgLAILCFLLASHLSTVKARGIKHRFKWNRKVLPSSGgQITEA****..
consensus  .........*........10........20........30........40.....

human      QVAENRPGAFIKQGRKLDIDFGAEGNRYYeANYWQFPDGIhYnGCSEANV****..
mouse      IVAENRPGAFIKQGRKLDIDFGAEGNRYYAANYWQFPDGIYYEGCSEANV****..
rat        QVAENRPGAFIKQGRKLDIDFGAEGNKYYAANYWQFPDGIYYEGCSEANV****..
consensus  .51......*........60........70........80........90.....

human      TKEafVTgCINATQAANQGEFq..KpDnKLHQqVLWRLvqELCSIKHCEF****..
mouse      TKEMLVTsCVNATQAANQAEFSREKQDSKLHQRVLWRLIKETCSAKHCDF****..
rat        TKEvLVTrCVNATQAANQAEFSREKQDSKLHQRVLWRLIKEICStKHCDF****..
consensus  .101.....*......120.......130.......140...

human      WLERGAGLRVTMhQPvLLCLLAiIW1MVK****..
mouse      WLERGAALRVaVDQPAMVCLLGFVWFIVK****..
rat        WLERGAALRItTVDQqAMVCLLGFIWFIVK****..
consensus  .151.....*.......160.......170...
```

FIGURE 7

```
euth._mammal_prp   ---MVMAHLGCW.MLVLF VATWSDLGLCKKR.PKPGGGWNTGGS.RYPGQ.
marsupial_prp      ---MGKIQLGYM.ILVLFIVTWSDLGLCKCKPKPRPGGGWNSGGSNRYPGQP
human_doppel       ---MRKHLSWWMLATVCMLLASELSAVQTRGIKHRIKWNRKALPSTA.Q.
mouse_doppel       ---MKERLGTWWVALLCMLLASELSTVHARGIKHRFKWNRKVLPSSGQ.
rat_doppel         ---MKNRLGTWGLAILCLLLASHLSTVHARGIKHRFKWNRKVLPSSG.Q.

euth._mammal_prp   GSPGGNRYPPPQGGGWGQGGWGQPHGGGWGQ..WGQPHGGGWGQPHGGGG
marsupial_prp      GSPGGNRYPGWGHPQGGGTN...WGQPHPGGSNWGQPHPGGSS.....WG
human_doppel       ..................................................
mouse_doppel       ..................................................
rat_doppel         ..................................................

euth._mammal_prp   WGQGGGGGWGQGGTHNQWNKPSKPKTNMKHMAGAAAAGAVVGGLGGYML.
marsupial_prp      QPHGG...SNWGQGG.YNKW.KPDKPKTNLKHVAGAAAAGAVVGGLGGYML.
human_doppel       ...........................ITEAQVAENRPGAFI.
mouse_doppel       ...........................ITEARVAENRPGAFI.
rat_doppel         ...........................ITEAQVAENRPGAFI.
                                                              A
euth._mammal_prp   GSAMSRPLIHFGNDYEDRYVRENMYRYPNQVYYRPV.DQYSNQNMFVHDC
marsupial_prp      GSAMSRPVIHFGNEYEDRYYRENQYRYPNQVMYRPI.DQYSQNMFVHDC
human_doppel       .KQGRKLDIDFGAEGN.RYYEANYWQFPDGIHYNGCSEANVTKEAFVTGC
mouse_doppel       .KQGRKLDIDFGAEGN.RYYAANYWQFPDGIYYEGCSEANVTKEMLVTSC
rat_doppel         .KQGRKLDIDFGAEGN.KYYAANYWQFPDGIYYEGCSEANVTKEVLVTRC
                                                              B
euth._mammal_prp   VNITIKQHTVTT.TT.KGENFNETBVKMLERVVEQMCITQYQRESQAYYQR
marsupial_prp      VNITVKQHTTTT.T..KGENFTETDIKIMERVVEQMCITQYQAEYEAAAQR
human_doppel       INATQAANQGEFQ..KPDNKLHQQV..LMRLVQELCSL...KHCEFWLER
mouse_doppel       VNATQAANQAEFSREKQDSKLHQRV..LMRLIKEICSA...KHCDFWLER
rat_doppel         VNATQAANQAEFSREKQDSKLHQRV..LMRLIKEICST...KHCDFWLER
                                                              C
euth._mammal_prp   GRSSMVFSSPPVILE.ISFLIFLIVG
marsupial_prp      ..AYNMAFFSAPPVTLFLSFLIFLIVS
human_doppel       GAGLRVTM.HQPVLCL.LALIWLMVK~
mouse_doppel       GAALRVAV.DQEAMVCL.LGFVWFIVK~
rat_doppel         GAALRITV.DQQAMVCL.LGFIWFIVK~
```

——— NMR helices

FIGURE 8

PRP-LIKE GENE

GOVERNMENT RIGHTS

The United States Government may have certain rights in this application pursuant to Grant No. NS 22786 awared by the National Institutes of Health.

FIELD OF THE INVENTION

This invention relates to nucleic acids, proteins encoded by such nucleic acids, and assays involving use of the these nucleic acids and/or proteins.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects one species of animal (e.g., a human) will not readily infect another (e.g., a mouse).

A major step in the study of prions and the diseases that they cause was the discovery and purification of a protein designated prion protein ("PrP") [Bolton et al., Science 218:1309–11 (1982); Prusiner et al., Biochemistry 21:6942–50 (1982); McKinley et al., Cell 35:57–62 (1983)]. Complete prion protein-encoding genes have since been cloned, sequenced and expressed in transgenic animals. $PrP^C$ is encoded by a single-copy host gene [Basler et al., Cell 46:417–28 (1986)] and is normally found at the outer surface of neurons. A leading hypothesis is that prion diseases result from conversion of $PrP^C$ into a modified form called $PrP^{Sc}$.

It appears that the scrapie isoform of the prion protein ($PrP^{Sc}$) is necessary for both the transmission and pathogenesis of the transmissible neurodegenerative diseases of animals and humans. See Prusiner, S. B., "Molecular biology of prion disease," Science 252:1515–1522 (1991). The most common prion diseases of animals are scrapie of sheep and goats and bovine spongiform encephalopathy (BSE) of cattle [Wilesmith, J. and Wells, Microbiol. Immunol. 172:21–38 (1991)]. Four prion diseases of humanes have been identified: (1) kuru, (2) Creutzfeldt-Jakob Disease (CJD), (3) Gerstmann-Strassler-Scheinker Disease (GSS), and (4) fatal familial insomnia (FFI) [Gajdusek, D. C., Science 197:943–960 (1977); Medori et al., N. Engl. J. Med. 326:444–449 (1992)]. The presentation of human prion diseases as sporadic, genetic and infectious illnesses initially posed a conundrum which has been explained by the cellular genetic origin of PrP.

Most CJD cases are sporadic, but about 10–15% are inherited as autosomal dominant disorders that are caused by mutations in the human PrP gene [Hsiao et al., Neurology 40:1820–1827 (1990); Goldfarb et al., Science 258:806–808 (1992); Kitamoto et al., Proc. R. Soc. Lond. 343:391–398. Iatrogenic CJD has been caused by human growth hormone derived from cadaveric pituitaries as well as dura mater grafts [Brown et al., Lancet 340:24–27 (1992)]. Despite numerous attempts to link CJD to an infectious source such as the consumption of scrapie infected sheep meat, none has been identified to date [Harries-Jones et al., J. Neurol. Neurosurg. Psychiatry 51:1113–1119 (1988)] except in cases of iatrogenically induced disease. On the other hand, kuru, which for many decades devastated the Fore and neighboring tribes of the New Guinea highlands, is believed to have been spread by infection during ritualistic cannibalism [Alpers, M. P., Slow Transmissible Diseases of the Nervous System, Vol. 1, S. B. Prusiner and W. J. Hadlow, eds. (New York: Academic Press), pp. 66–90 (1979)].

The initial transmission of CJD to experimental primates has a rich history beginning with William Hadlow's recognition of the similarity between kuru and scrapie. In 1959, Hadlow suggested that extracts prepared from patients dying of kuru be inoculated into nonhuman primates and that the animals be observed for disease that was predicted to occur after a prolonged incubation period [Hadlow, W. J., Lancet 2:289–290 (1959)]. Seven years later, Gajdusek, Gibbs and Alpers demonstrated the transmissibility of kuru to chimpanzees after incubation periods ranging form 18 to 21 months [Gajdusek et al., Nature 209:794–796 (1966)]. The similarity of the neuropathology of kuru with that of CJD [Klatzo et al., Lab Invest. 8:799–847 (1959)] prompted similar experiments with chimpanzees and transmissions of disease were reported in 1968 [Gibbs, Jr. et al., Science 161:388–389 (1968)]. Over the last 25 years, about 300 cases of CJD, kuru and GSS have been transmitted to a variety of apes and monkeys.

The expense, scarcity and often perceived inhumanity of such experiments have restricted this work and thus limited the accumulation of knowledge. While the most reliable transmission data has been said to emanate from studies using nonhuman primates, some cases of human prion disease have been transmitted to rodents but apparently with less regularity [Gibbs, Jr. et al., Slow Transmissible Diseases of the Nervous System, Vol. 2, S. B. Prusiner and W. J. Hadlow, eds. (New York: Academic Press), pp. 87–110 (1979); Tateishi et al., Prion Diseases of Humans and Animals, Prusiner et al., eds. (London: Ellis Horwood), pp. 129–134 (1992)].

The importance of understanding the conversion of $PrP^C$ into $PrP^{Sc}$ has been heightened by the possibility that bovine prions have been transmitted to humans who developed variant Creutzfeldt-Jakob disease (vCJD), G. Chazot, et al., Lancet 347:1181 (1996); R. G. Will, et al., Lancet 347:921–925 (1996). Earlier studies had shown that the N-terminus of $PrP^{Sc}$ could be truncated without loss of scrapie infectivity, S. B. Prusiner, et al., Biochemistry 21:6942–6950 (1982); S. B. Prusiner, et al., Cell 38:127–134 (1984) and correspondingly, the truncation of the N-terminus of $PrP^{Sc}$ still allowed its conversion into $PrP^{Sc}$ M. Rogers, et al., Proc. Natl. Acad. Sci. USA 90:3182–3186 (1993).

Recent studies have advanced the ability to visualize the structural transition of $PrP^C$ to $PrP^{Sc}$ at a molecular level. For example, the N-terminal portion is relatively unstructured and flexible, but assists in stabilizing structural elements within the C-terminal portion. D. G. Donne et al., Proc. Natl. Acad. Sci. USA 94:13452–13457 (1997). Furthermore, immunological studies have demonstrated that N-terminal epitopes are cryptic in $PrP^{Sc}$, supporting the idea that this region undergoes profound conformational change during prion propagation. Peretz et al., J. Mol. Biol. 273:614–622 (1997).

Despite these advances, the understanding of the structural biology of the pathogenic conversion process remains incomplete in many ways. For example, it is unknown exactly which structural regions of $PrP^C$ are necessary or sufficient for conformational change to occur. It is also unknown which regions of $PrP^{Sc}$ are necessary or sufficient for infectivity. Evidence indicates that prion strain phenomena and species barriers are encoded by alternative PrP conformations, but the precise structural determinants of these conformations have not yet been precisely identified. Telling et al. *Science* 274:2079–2082 (1996); Billeter, et al., *Proc. Natl. Acad. Sci. USA* 94:7281–7285 (1997). Recent studies have identified four residues of mouse PrP (MoPrP) that appear to interact with protein X, a putative factor postulated to facilitate the conformational change from $PrP^C$ to $PrP^{Sc}$. Telling, et. al. *Cell* 83:79–90 (1995). All four amino acids come together to form the putative protein X binding site in the tertiary structure of recombinant PrIP 90-231 and PrIP 29-231. D. G. Donne et al., *Proc. Natl. Acad. Sci. USA* 94:13452–13457 (1997); T. L. James et al., *Proc. Natl. Acad. Sci. USA* 94:10086–10091 (1997). However, despite several reports of proteins which bind $PrP^C$, the identity of protein X remains elusive. Finally, although the structures of refolded, recombinant PrP molecules may resemble $PrP^C$, a structural solution for $PrP^{Sc}$ remains lacking.

One strategy for determining PrP function is through the identification of proteins similar to PrP, and the elucidation of the function of such proteins. The identification and study of prion-related genes may offer insight into the general biology and progression of neurodegenerative disorders, as well as offering insight into the mechanistic alterations that result in prion-mediated disorders. There is thus a need in the art for the identification and study of genes encoding proteins with similar structure and/or function.

SUMMARY OF THE INVENTION

The present invention provides nucleic acids encoding the Doppel ("Dpl") protein, Dpl peptides, and assays utilizing the Dpl nucleic acids and/or peptides. In a particular aspect, the Dpl protein is encoded by the nucleotide sequence of SEQ ID NO:1 and degenerate sequences thereof. In addition, the invention features isolated nucleic acid sequences comprising a Dpl promoter, as well as nucleic acid sequences that hybridize under stringent conditions to SEQ ID NO:1. In related aspects the invention features expression vectors and host cells comprising nucleic acids that encode a human Dpl polypeptide. The present invention also relates to antibodies that bind specifically to a human Dpl polypeptide, methods for producing human Dpl polypeptides, methods for identifying cells expressing Dpl, methods for using the Dpl gene and the Dpl polypeptide to alter cellular function and prion infectivity in culture or in vivo, and identification of individuals at risk for degenerative disorders by detecting alteration in Dpl coding and regulatory sequences and Dpl expression levels.

A primary object of the invention is to provide an isolated human Dpl polypeptide-encoding nucleic acids for use in expression of human Dpl (e.g, in a recombinant host cell) and for use in, for example, identification of human Dpl polypeptide binding compounds (especially those compounds that affect human Dpl polypeptide-mediated activity, which compounds can be used to modulate Dpl activity).

Another object of the invention is to provide an isolated human Dpl polypeptide-encoding nucleic acid for use in generation of non-human transgenic animal models for Dpl gene function, particularly "knock-in" Dpl non-human transgenic animals characterized by excess or ectopic expression of the Dpl gene.

In particular, Dpl appears to have a synergistic interaction with the products of the PrP locus, and mutations in the Dpl locus decreases the incubation period of animals infected with the scrapie form of PrP, $PrP^{Sc}$. DNA encoding Dpl is also disclosed for use of the DNA expression product in an assay to modulate the incubation time needed for prion-mediated disorders, as well as to identify compounds that modulate the incubation time necessary for the measurable onset of symptoms of prion infection.

The invention also features DNA sequences that hybridize under stringent conditions to DNA encoding Dpl, or to DNA complementary to DNA encoding Doppel. Such DNA sequences are preferably at least 25 nucleotides in length, more preferably 50 nucleotides in length. Peptide fragments of Dpl, e.g. those useful in assays, are preferably at least 10 amino acids in length, more preferably at least 30 amino acids in length.

The invention also features chimeric Dpl genes having sequences from both a host animal and a genetically diverse animal, and transgenic animals containing such genes.

An object of the invention is to provide a nucleotide sequence encoding a novel Dpl protein and its functional equivalents.

Another object is to provide a cell line genetically engineered to express the nucleotide sequence encoding Dpl.

Another object is to provide an antibody which selectively binds to the Dpl protein or peptides thereof.

Another object is to provide a method whereby a compound or library of compounds can be assayed for their ability to activate or block the activity of the protein expressed by the Dpl nucleotide sequence.

An advantage of the present invention is that mutations that increase Dpl activity and/or expression accelerate prion infection, thus allowing an earlier identification of prion infectivity from an inoculum in animal assays, e.g. in transgenic HuPrP mouse assays.

An aspect of the invention is transgenic mice expressing (1) human Dpl; (2) human Dpl and human PrP; (3) human/mouse chimeric genes for Dpl and PrP; (4) bovine Dpl; (5) bovine Dpl and bovine PrP; (6) bovine/mouse chimeric genes for Dpl and PrP; (7) combination of (1–6) with an ablated endogeneous Dpl and/or PrP gene; (7) sheep Dpl; (8) goat Dpl; (9) elk Dpl; and (10) deer Dpl. Transgenic mice that may be used in the present invention are described in U.S. Pat. No. 5,565,186 issued Oct. 15, 1996, U.S. Pat. No. 5,763,740 issued Jun. 9, 1998, U.S. Pat. No. 5,789,655 issued Aug. 4, 1998, and U.S. Pat. No. 5,792,901, issued Aug. 11, 1998, which are incorporated by reference herein.

These and other objects, advantages and features of the present invention will become apparent to those skilled in the art upon reading the disclosure.

BRIEF DESCRIPTION OF THE DRAWINGS

FIG. 1A is a schematic diagram illustrating the genomic structure and coding regions of the Dpl (PrnD) gene locus.

FIG. 1B illustrates the splice variants of Dpl, as well as identified ESTs in this region.

FIGS. 2A–2E are the nucleotide and corresponding amino acid sequence of the mouse Dpl gene.

FIG. 3 is a schematic diagram illustrating the alternative splice donor sites of Exon 1.

FIG. 4 is a structural overview of Prn gene region, with the most abundant forms Prnp and PrnD spliced mRNAs (thin lines) shown at the top of the figure. Chimeric cDNAs are shown in bold lines, with the positions of oligonucleotide primers (arrows) used for RT-PCR shown above the chromosomal gene.

FIG. 5 is a schematic diagram illustrating the structure of Dpl cDNA varieties Prnp exon 2 and PrnD exon 2 sequences common to all cDNAs are shown by bold cross-hatch and open boxes, respectively.

FIG. 6 is a schematic diagram illustrating the structures of PrP gene disruptions in four lines of Prnp$^{0/0}$ mice. The large black arrows indicate the alleles which delete the exon 3 splice acceptor and are associated with the development of a late-onset ataxia. A small vertical arrow indicates the position of the exon 3 splice acceptor deleted in the Ngsk and Rcm alleles. The open box is the PrP coding region and the gray box is the PrP UTR. Enzymes are as follows: E, Eco RI; X, Xba I; K, Kpn I.

FIGS. 7 and 8 illustrate multiple sequence alignment of human (SEQ ID NO:2), mouse (SEQ ID NO:3) and rat (SEQ ID NO:4) Dpl with representative PrP molecules showing the regions of identity and conservation.

Figure 9:
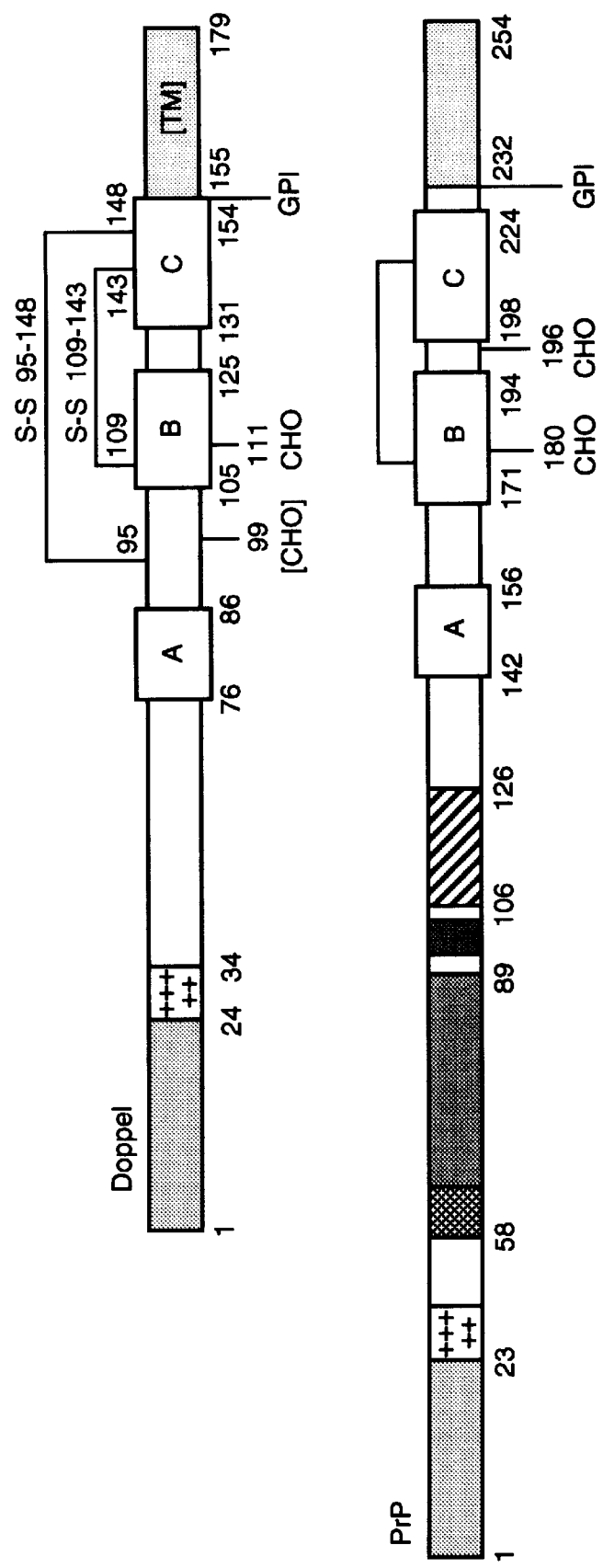

FIG. 9 is a schematic of the Dpl and PrP protein structure showing the positions of the predicted features of each. Three alpha helices found in PrP are shown as grey boxes with A, B and C representing the three predicted Dpl helices. The white box with the + symbols indicate a cluster of basic residues.

DETAILED DESCRIPTION OF PREFERRED EMBODIMENTS

Before the present DNA molecule, proteins, and methods of use are described, it is to be understood that this invention is not limited to particular molecules described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "nucleic acid" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "nucleic acid" is used to refer to a specific nucleic acid sequence (e.g. a Dpl polypeptide-encoding nucleic acid), "nucleic acid" is meant to encompass nucleic acids that encode a polypeptide that is functionally equivalent to the recited polypeptide, e.g., nucleic acids that are degenerate variants, or nucleic acids that encode biologically active variants or fragments of the recited polypeptide. Similarly, "polypeptide" as used herein refers to an oligopeptide, peptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule.

By "antisense nucleic acid" is mean a nucleic acid having a nucleotide sequence complementary to a given nucleic acid sequence (e.g, a nucleic acid sequence encoding a Dpl polypeptide) including nucleic acid sequences associated with the transcription or translation of the given nucleic acid sequence (e.g., a promoter of a nucleic acid encoding a Dpl polypeptide), where the antisense nucleic acid is capable of hybridizing to a Dpl polypeptide-encoding nucleic acid sequence. Of particular interest are antisense nucleic acids capable of inhibiting transcription and/or splicing and/or translation of a Dpl-encoding nucleic acid either in vitro or in vivo.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen et al., *Anticancer Drug Des* 8:53–63 (1993)).

By a "polypeptide" is meant any chain of amino acids, regardless of length or post-translational modification (e.g., glycosylation).

As used herein, "Dpl polypeptide" refers to an amino acid sequence of a recombinant or nonrecombinant polypeptide having an amino acid sequence of i) a native Dpl polypeptide, ii) a biologically active fragment of a Dpl polypeptide, iii) biologically active polypeptide analogs of a Dpl polypeptide, or iv) a biologically active variant of a Dpl polypeptide. Dpl polypeptides of the invention can be obtained from any species, e.g., mammalian or non-mammalian (e.g., reptiles, amphibians, avian (e.g., chicken)), particularly mammalian, including human, rodent (e.g., murine or rat), bovine, ovine, porcine, murine, or equine, preferably rat or human, from any source whether natural, synthetic, semi-synthetic or recombinant. "Human Dpl polypeptide" refers to the amino acid sequences of isolated human Dpl polypeptide obtained from a human, and is meant to include all naturally-occurring allelic variants, and is not meant to limit the amino acid sequence to the complete, native amino acid sequence associated with the recited protein molecule.

As used herein, "antigenic amino acid sequence" means an amino acid sequence that, either alone or in association with a carrier molecule, can elicit an antibody response in a mammal.

A "variant" of a human Dpl polypeptide is defined as an amino acid sequence that is altered by one or more amino acids. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which and how many amino acid residues may be substituted, inserted or deleted without abolishing biological or immunological activity can be found using computer programs well known in the art, for example, DNAStar software.

A "deletion" is defined as a change in either amino acid or nucleotide sequence in which one or more amino acid or nucleotide residues, respectively, are absent as compared to an amino acid sequence or nucleotide sequence of a naturally occurring Dpl polypeptide.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring Dpl polypeptide.

A "substitution" results from the replacement of one or more amino acids or nucleotides by different amino acids or nucleotides, respectively as compared to an amino acid sequence or nucleotide sequence of a naturally occurring Dpl polypeptide.

The term "biologically active" refers to human Dpl polypeptide having structural, regulatory, or biochemical functions of a naturally occurring Dpl polypeptide. Likewise, "immunologically active" defines the capability of the natural, recombinant or synthetic human Dpl polypeptide, or any oligopeptide thereof, to induce a specific immune response in appropriate animals or cells and to bind with specific antibodies.

The term "derivative" as used herein refers to the chemical modification of a nucleic acid encoding a human Dpl polypeptide or the encoded human Dpl polypeptide. Illustrative of such modifications would be replacement of hydrogen by an alkyl, acyl, or amino group. A nucleic acid derivative would encode a polypeptide which retains essential biological characteristics of a natural Dpl polypeptide.

As used herein the term "isolated" is meant to describe a compound of interest (e.g., either a nucleic acid or a polypeptide) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound (e.g., either a nucleic acid or a polypeptide) that is removed from its natural environment and is at least 60% free, preferably 75% free, and most preferably 90% free from other components with which it is naturally associated.

"Stringency" typically occurs in a range from about Tm-5° C. (5° C. below the Tm of the probe) to about 20° C. to 25° C. below Tm. As will be understood by those of skill in the art, a hybridization stringency can be manipulated to identify or detect identical nucleic acid sequences or to identify or detect similar or related nucleic acid sequences.

The term "hybridization" as used herein shall include "any process by which a strand of nucleic acid joins with a complementary strand through base pairing" (Coombs, *Dictionary of Biotechnology*, Stockton Press, New York N.Y. (1994)). Amplification as carried out in the polymerase chain reaction technologies is described in Dieffenbach et al., *PCR Primer, a Laboratory Manual*, Cold Spring Harbor Press, Plainview N.Y. (1995).

By "transformation" is meant a permanent or transient genetic change, preferably a permanent genetic change, induced in a cell following incorporation of new DNA (i.e., DNA exogenous to the cell). Genetic change can be accomplished either by incorporation of the new DNA into the genome of the host cell, or by transient or stable maintenance of the new DNA as an episomal element. Where the cell is a mammalian cell, a permanent genetic change is generally achieved by introduction of the DNA into the genome of the cell.

By "construct" is meant a recombinant nucleic acid, generally recombinant DNA, that has been generated for the purpose of the expression of a specific nucleotide sequence(s), or is to be used in the construction of other recombinant nucleotide sequences.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest (i.e., facilitates the production of, e.g., a polypeptide encoded by a Dpl sequence).

By "Dpl associated disorder" is meant a physiological condition or disease associated with altered Dpl function (e.g., due to aberrant Dpl expression or a defect in Dpl expression or in the Dpl protein). Such Dpl associated disorders can include, but are not necessarily limited to, prion-like disorders or other similar disorders that involve neurotoxicity and/or neurodegeneration.

The term "transgene" is used herein to describe genetic material which has been or is about to be artificially inserted into the genome of a mammalian, particularly a mammalian cell of a living animal.

By "transgenic organism" is meant a non-human organism (e.g., single-cell organisms (e.g., yeast), mammal, non-mammal (e.g., nematode or Drosophila)) having a non-endogenous (i.e., heterologous) nucleic acid sequence present as an extrachromosomal element in a portion of its cells or stably integrated into its germ line DNA.

By "transgenic animal" is meant a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal. A mouse is a preferred transgenic animal.

A "knock-out" of a target gene means an alteration in the sequence of the gene that results in a decrease of function of the target gene, preferably such that target gene expression is undetectable or insignificant. A knock-out of a Dpl gene means that function of the Dpl gene has been substantially decreased so that Dpl expression is not detectable or only present at insignificant levels. "Knock-out" transgenics of the invention can be transgenic animals having a heterozygous knock-out of the Dpl gene or a homozygous knock-out of the Dpl gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic) or decreased expression) of the target gene, e.g., by introduction of an additional copy of the target gene, or by operatively inserting a regulatory sequence that provides for enhanced expression of an endogenous copy of the target gene. "Knock-in" transgenics of the invention can be transgenic animals having a heterozygous knock-in of the Dpl gene or a homozygous knock-in of the Dpl gene. "Knock-ins" also encompass conditional knock-ins.

The term "Prnp$^{0/0}$ or Prnp-Abl" refers to a transgenic animal which has its PrP gene ablated with the "$^{0/0}$" indicating that both alleles are ablated whereas o/+ indicates only one is ablated. Specifically, the animal being referred to is generally a transgenic mouse which has its PrP gene ablated i.e., a PrP knockout mouse. In that the PrP gene is disrupted, no mouse PrP protein is expressed.

The term "prion" shall mean an infectious particle known to cause diseases (spongiform encephalopathies) in animals including cows and humans. The term "prion" is a contraction of the words "protein" and "infection" and the particles are comprised largely if not exclusively of PrP$^{Sc}$ molecules encoded by a PrP gene. Prions are distinct from bacteria, viruses and viroids. Known prions include those which infect animals to cause scrapie, a transmissible, degenerative disease of the nervous system of sheep and goats as well as bovine spongiform encephalopathies (B SE) or "mad cow" disease and feline spongiform encephalopathies of cats. Four prion diseases known to affect humans are (1) kuru, (2) Creutzfeldt-Jakob Disease (CJD), (3) Gerstmann-Sträussler-Scheinker Disease (GSS), and (4) fatal familial insomnia (FFI). As used herein prion includes all forms of prions causing all or any of these diseases or others in any animals used—and in particular in humans, cows and other domesticated farm animals.

The terms "PrP gene" and "Prnp gene" are used interchangeably herein to describe genetic material which expresses proteins (for example those shown in FIGS. 3–5 of U.S. Pat. No. 5,565,186 issued Oct. 15, 1996) and polymorphisms and mutations such as those listed herein under the subheading "Pathogenic Mutations and Polymorphisms." The PrP gene can be from any animal including the "host" and "test" animals described herein and any and all polymorphisms and mutations thereof, it being recognized that the terms include other such PrP genes that are yet to be discovered.

The term "artificial PrP gene" is used herein to encompass the term "chimeric PrP gene" as well as other recombinantly constructed genes which when included in the genome of a host animal (e.g., a mouse) will render the mammal susceptible to infection from prions which naturally only infect a genetically diverse test mammal, e.g., human, bovine or ovine. In general, an artificial gene will include the codon sequence of the PrP gene of the mammal being genetically altered with one or more (but not all, and generally less than 40) codons of the natural sequence being replaced with a different codon—preferably a corresponding codon of a genetically diverse mammal (such as a human). The genetically altered mammal being used to assay samples for prions which only infect the genetically diverse mammal. Examples of artificial genes are mouse PrP genes encoding the sequence as shown in FIGS. 3, 4 and 5 of U.S. Pat. No. 5,565,186 with one or more different replacement codons selected from the codons shown in these Figures for humans, cows and sheep replacing mouse codons at the same position, with the proviso that not all the mouse codons are replaced with differing human, cow or sheep codons. Artificial PrP genes of the invention can include not only codons of genetically diverse animals but may include codons and codon sequences associated with genetic prion diseases such as CJD and codons and sequences not associated with any native PrP gene but which, when inserted into an animal render the animal susceptible to infection with prions which would normally only infect a genetically diverse animal.

The terms "chimeric gene," "chimeric PrP gene" and the like are used interchangeably herein to mean an artificially constructed gene containing the codons of a host animal such as a mouse with one or more of the codons being replaced with corresponding codons from a genetically diverse test animal such as a human, cow or sheep. In one specific example the chimeric gene is comprised of the starting and terminating sequence (i.e., N- and C-terminal codons) of a PrP gene of a mammal of a host species (e.g. a mouse) and also containing a nucleotide sequence of a corresponding portion of a PrP gene of a test mammal of a second species (e.g. a human). A chimeric gene will, when inserted into the genome of a mammal of the host species, render the mammal susceptible to infection with prions which normally infect only mammals of the second species. The preferred chimeric gene disclosed herein is MHu2M which contains the starting and terminating sequence of a mouse PrP gene and a non-terminal sequence region which is replaced with a corresponding human sequence which differs from a mouse PrP gene in a manner such that the protein expressed thereby differs at nine residues.

The terms "host animal" and "host mammal" are used to describe animals which will have their genome genetically and artificially manipulated so as to include genetic material which is not naturally present within the animal. For example, host animals include mice, hamsters and rats which have their endogenous PrP gene altered by the insertion of an artificial gene of the present invention or by the insertion of a native PrP gene of a genetically diverse test animal.

The terms "host animal" and "host mammal" are used to describe animals which will have their genome genetically and artificially manipulated so as to include genetic material which is not naturally present within the animal. For example, host animals include mice, hamsters and rats which have their endogenous Dpl gene altered. In a preferred embodiment, these host animals also have a PrP gene altered by the insertion of an artificial gene or by the insertion of a native PrP gene of a genetically diverse test animal.

The terms "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions with which the test animal would generally be susceptible to infection. For example, the test animal may be a human, cow, sheep, pig, horse, cat, dog, turkey or chicken, and one may wish to determine whether a particular sample includes prions which would normally only infect the test animal. This is done by including PrP gene sequences of the test animal into the host animal and inoculating the host animal with prions which would normally only infect the test animal.

The terms "genetically diverse animal" and "genetically diverse mammal" are used to describe an animal which includes a native PrP codon sequence of the host animal which differs from the genetically diverse test animal by 17 or more codons, preferably 20 or more codons, and most preferably 28–40 codons. Thus, a mouse PrP gene is genetically diverse with respect to the PrP gene of a human, cow or sheep, but is not genetically diverse with respect to the PrP gene of a hamster.

The terms "ablated PrP gene", "disrupted PrP gene" and the like are used interchangeably herein to mean an endogenous PrP gene which has been altered (e.g., add and/or remove nucleotides) in a manner so as to render the gene inoperative. Examples of non-functional PrP genes and methods of making such are disclosed in Bueler, et al, *Nature* 356:577–582 (1992) which is incorporated herein by reference. Both alleles of the genes are preferably disrupted.

The terms "ablated Dpl gene", "disrupted Dpl gene" and the like are used interchangeably herein to mean an endogenous Dpl gene which has been altered (e.g., add and/or remove nucleotides) in a manner so as to render the gene inoperative.

The terms "hybrid animal", "transgenic hybrid animal" and the like are used interchangeably herein to mean an animal obtained from the cross-breeding of a first animal having altered Dpl activity and a second animal which includes (1) an ablated endogenous PrP gene (1) a chimeric or artificial PrP gene and/or (3) a PrP gene from a genetically diverse animal. For example a hybrid mouse is obtained by cross-breeding a mouse having a Dpl transgene knock-in with a mouse containing (1) bovine PrP genes (which may be present in high copy numbers) alone or with (2) chimeric PrP genes. In another example, a hybrid mouse can be obtained by cross-breeding a $PrP^{0/0}$ mouse with unregulated Dpl activity and a mouse having an inducible exogenous human PrP gene. The term hybrid includes any offspring of a hybrid including inbred offspring of two hybrids provided the resulting offspring is susceptible to infection with prions with normal infect only a genetically diverse species and the symptoms of the infection are observable in about 350 days or less, preferably 250 or less.

The term "incubation time" shall mean the time from inoculation of an animal with a prion until the time when the animal first develops detectable symptoms of disease resulting from the infection. A reduced incubation time is preferably about 200 days±50 days or less, more preferably about 50 days±20 days or less.

By "antibody" is meant an immunoglobulin protein which is capable of binding an antigen. Antibody as used herein is meant to include the entire antibody as well as any antibody fragments (e.g. $F(ab')_2$, Fab', Fab, Fv) capable of binding the epitope, antigen or antigenic fragment of interest.

Antibodies of the invention are immunoreactive or immunospecific for and therefore specifically and selectively bind to a Dpl protein. Antibodies for Dpl are preferably immunospecific—i. e., not substantially cross-reactive with related materials. Although the term "antibody" encompasses all types of antibodies (e.g., monoclonal) the antibodies of the invention are preferably produced using the phage display methodology described herein. The preferred antibody of the invention is a purified antibody. By purified antibody is meant one which is sufficiently free of other proteins, carbohydrates, and lipids with which it is naturally associated. Such an antibody "preferentially binds" to a Dpl protein (or an antigenic fragment thereof), i.e., does not substantially recognize and bind to other antigenically-unrelated molecules.

By "specifically activates", as used herein, is meant an agent which activates Dpl or a fragment or analog thereof to initiate Dpl-mediated biological events as described herein, but which does not substantially bind other molecules in a sample, e.g., a biological sample.

By "specifically inhibits", as used herein, is meant an agent which inhibits activation of Dpl or a polypeptide, fragment or analog thereof Preferably, the agent activates or inhibits the biological activity in vivo or in vitro of the protein to which it binds.

By "substantial increase" is meant an increase in activity or other measurable phenotypic characteristic that is at least approximately a 2-fold increase over control level (where control assays are performed in the absence of activator), preferably at least approximately a 5-fold increase, more preferably at least approximately a 10-fold increase in activity over a control assay.

By "substantial decrease" or "substantial reduction" is meant a decrease or reduction in activity or other measurable phenotypic characteristic that is approximately 80% of the control level, preferably reduced to approximately 50% of the control level, or more preferably reduced to approximately 10% or less of the control level.

The terms "screening method" and "assay method" are used to describe a method of screening a candidate compound for its ability to act as an activator or suppressor of 1) Dpl activity and/or 2) prion infection incubation time.

The terms "treatment", "treating", "treat" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particular a human, and includes:

(a) preventing the disease or symptom from occurring in a subject which may be predisposed to the disease or symptom but has not yet been diagnosed as having it;

(b) inhibiting the disease symptom, i.e., arresting its development; or (c) relieving the disease symptom, i.e., causing regression of the disease.

GENERAL ASPECTS OF THE INVENTION

Described herein is a novel 179 residue protein designated Dpl (Dpl) with ~25% identity to all known prion proteins (PrP). Since database searches to identify PrP-like genes failed to be informative, and hybridization studies were not fruitful in such efforts (Westaway et al., *Nucleic Acids Res.* 14:2035–2044 (1986)), the sequencing of large cosmid clones containing the PrP gene was undertaken (Lee et al., *Genome Res.* 8:1022–1037 (1998)). While most vertebrate genes of related function are not arranged in clusters, some related genes are. In studies of the regions around the human, sheep and mouse PrP genes, no additional open reading frames (ORF) were identified. Only when the sequencing of a cosmid clone isolated from a $Pmp^{b/b}$ (ILN/J) mouse was extended downstream of PrP was a novel ORF found.

The Dpl locus, called "Prnd" is 16 Kb downstream of the PrP gene Prnp and produces two major transcripts of 1.7 and 2.7 Kb as well as some unusual chimeric transcripts generated by intergenic splicing with Prnp. Polycistronic mRNA between PrP and Dpl have also been identified. Like PrP, Dpl mRNA is expressed during embryogenesis but in contrast to PrP, it is expressed at low levels in the CNS but at high levels in the testis. Dpl is unregulated in the CNS of the two $Prnp^{0/0}$ lines that develop a late-onset ataxia and Purkinje cell degeneration, but not in a $Prnp^{0/0}$ line that does not develop ataxia. The Dpl may be neurotoxic which explains why some lines of $Prnp^{0/0}$ mice develop neurodegeneration. Dpl may also be toxic to other non neuronal cell types.

Moreover, the substantial homology between Dpl and PrP suggests these two proteins may share some biological properties and as such, Dpl may comprise a new element for understanding prion biology. By identifying Prnd as the first candidate for a PrP-like gene, we have begun to define the Prn gene family. Interestingly, overexpression of Dpl, like some mutant and foreign PrPs, produces neurodegeneration in the CNS of mice. In addition, Dpl and PrP may interact directly or indirectly by competing as ligands for a common receptor protein. The invention described herein provides a means for testing these hypotheses.

Dpl Nucleic Acid

The terms "Dpl gene" and "Prnd" are used generically to designate the coding region of Dpl. "Dpl gene" and "Prnd" are also intended to mean the open reading frame encoding specific Dpl polypeptides, introns, and adjacent 5' and 3' non-coding nucleotide sequences involved in the regulation of expression, up to about 1 kb beyond the transcribed region, but possibly further in either direction. The DNA sequences encoding Dpl may be cDNA or genomic DNA or a fragment thereof. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons (e.g., sequences encoding open reading frames of the encoded polypeptide) and 3' and 5' non-coding regions. Normally mRNA species have contiguous exons, with the intervening introns removed by nuclear RNA splicing, to create a continuous open reading frame encoding the Dpl polypeptide.

While other genomic Dpl sequences of other sources may have non-contiguous open reading frames (e.g., where introns interrupt the protein coding regions), the human genomic Dpl sequence has no introns interrupting the coding sequence. A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where Dpl is expressed. The sequences of the Dpl promoter elements of the invention can be based on the nucleotide sequences of any species (e.g., mammalian or non-mammalian (e.g., reptiles, amphibians, avian (e.g., chicken)), particularly mammalian, including human, rodent (e.g., murine or rat), bovine, ovine, porcine, murine, or equine, preferably rat or human) and can be isolated or produced from any source whether natural, synthetic, semi-synthetic or recombinant.

The tissue specific expression of Dpl is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al., *Mol Med* 1:194–205 (1995); Mortlock et al., *Genome Res.* 6: 327–33 (1996); and Joulin et al., *Eur J Biochem* 232: 620–626 (1995).

In one embodiment, the promoter is used to modulate Dpl expression. As discussed below, Dpl is expressed in embryonic cardiac tissue and a subset of neurons in the adult brain. Thus, the developmentally timed expression directed by the Dpl promoter can be exploited to facilitate expression of heterologous genes operably linked to the Dpl promoter. Exemplary genes of interest that can be expressed from the Dpl promoter include, but are not necessarily limited to: marker genes (e.g., for marking the neuronal cells expressing Dpl) and reporter genes (e.g., luciferase, CAT, etc.) Such marker and reporter genes can be used to aid in elucidation of Dpl's normal physiological function, in identifying mechanisms for regulating Dpl and/or to search for bioactive agents (e.g., candidate pharmaceutical agents) that regulate Dpl expression, and the like.

The regulatory sequences may be used to identify cis acting sequences required for transcriptional or translational regulation of Dpl expression, especially in different tissues or stages of development, and to identify cis acting sequences and trans acting factors that regulate or mediate Dpl expression. Such transcriptional or translational control regions may be operably linked to a Dpl gene or other genes in order to promote expression of wild type or altered Dpl or other proteins of interest in cultured cells, or in embryonic, fetal or adult tissues, and for gene therapy. Dpl transcriptional or translational control regions can also be used to identify extracellular signal molecules that regulate Dpl promoter activity, and thus regulate Dpl expression.

The nucleic acid compositions used in the subject invention may encode all or a part of the Dpl polypeptides as appropriate. The Dpl sequences may be directed to forms of Dpl associated with disease states and/or to naturally occurring variants of the protein. Fragments may be obtained of the DNA sequence by chemically synthesizing oligonucleotides in accordance with conventional methods, by restriction enzyme digestion, by PCR amplification, etc. For the most part, DNA fragments will be of at least about ten contiguous nucleotides, usually at least about 15 nt, more usually at least about 18 nt to about 20 nt, more usually at least about 25 nt to about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The Dpl gene is isolated and obtained in substantial purity, generally as other than an intact mammalian chromosome. Usually, the DNA will be obtained substantially free of other nucleic acid sequences that do not include a Dpl sequence or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They may be used as probes for identifying other genes encoding prion-like proteins, or for identifying Dpl homologs in various species. Mammalian homologs have substantial sequence similarity to one another, i.e. at least 75%, usually at least 90%, more usually at least 95% sequence identity. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al., *J Mol Biol* 215:403–10 (1990).

Nucleic acids having sequence similarity are detected by hybridization under low stringency conditions, for example, at 50° C. and 6×SSC (0.9 M saline/0.09 M sodium citrate) and remain bound when subjected to washing at 55° C. in 1×SSC (0.15 M sodium chloride/0.015 M sodium citrate). Sequence identity may be determined by hybridization under high stringency conditions, for example, at 50° C. or higher and 0.1×SSC (15 mM saline/0.15 mM sodium citrate). By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, Drosophila, Caenhorabditis, etc.

The Dpl-encoding DNA may also be used to identify expression of the gene in a biological specimen. The manner in which one probes cells for the presence of particular nucleotide sequences, as genomic DNA or RNA, is well established in the literature and does not require elaboration here. mRNA is isolated from a cell sample. mRNA may be amplified by RT-PCR, using reverse transcriptase to form a complementary DNA strand, followed by polymerase chain reaction amplification using primers specific for the subject DNA sequences. Alternatively, mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to a Dpl sequence is indicative of Dpl gene expression in the sample.

The Dpl nucleic acid sequence may be modified for a number of purposes, particularly where they will be used intracellularly, for example, by being joined to a nucleic acid cleaving agent, e.g. a chelated metal ion, such as iron or chromium for cleavage of the gene, or the like.

The sequence of the Dpl locus, including flanking promoter regions and coding regions, may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g with the FLAG system, HA, etc. For studies of subcellular localization, fusion proteins with green fluorescent proteins (GFP) may be used. Such mutated genes may be used to study structure-function relationships of Dpl polypeptides with other polypeptides (e.g., Nkx-6.1, which is co-expressed with Dpl), or to alter properties of the proteins that affect their function or regulation. Such modified Dpl sequences can be used to, for example, generate the transgenic animals.

Techniques for in vitro mutagenesis of cloned genes are known. Examples of protocols for scanning mutations may be found in Gustin et al., *Biotechniques* 14:22 (1993); Barany, *Gene* 37:111–23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual*, CSH Press, pp. 15.3–15.108 (1989); Weiner et al., *Gene* 126:35–41 (1993); Sayers et al., *Biotechniques* 13:592–6 (1992); Jones et al., *Biotechniques* 12:528–30 (1992); Barton et al., *Nucleic Acids Res* 18:7349–55 (1990); Marotti et al., *Gene Anal Tech* 6:67–70 (1989); and Zhu, *Anal Biochem* 177:120–4 (1989).

Dpl gene comprising portions of the host animal e.g., end portions of a host animal and a middle portion of a genetically diverse test animal wherein the middle portion includes a specific alterations designed to match that of a disease state of such a host. Further, the invention includes, a transgenic animal containing the artificial gene or modulated expression of a Dpl gene from a genetically diverse animal, hybrid transgenic animals which are the offspring of different transgenic animals with each other or with a transgenic animal that has an ablated endogenous prion protein gene, a standardized prion preparation and assay methodology which uses the preparation and genetically altered animals to detect pathogenic prions in a sample.

The artificial gene includes a sequence such that when it is inserted into the genome of an animal (such as a mouse), the animal is rendered susceptible to infection with prions which normally would infect only a specific species of genetically diverse animal (such as a human, cow, sheep, pig, chicken, cat or dog). The artificial Dpl gene may be comprised partially or completely of an artificial polynucleotide sequence, i.e. codon sequences not present in any native Dpl gene sequence. Alternatively, the artificial gene may be comprised of the codon sequence of a host animal with one or more codon substitutions being made wherein the substitutions are preferably corresponding Dpl gene codons from a genetically diverse animal, meaning that Dpl gene differs from the Dpl gene of the host animal by 20 or more codons. Transgenic animals containing elevated levels of expression of the Dpl gene which can be obtained for example, by over expression of the gene with an enhanced promoter and/or with high copy numbers of the natural Dpl gene of a genetically diverse animal are also disclosed. Hybrid transgenic animals include animals resulting from a cross between two transgenic animals and in particular a cross between a transgenic animal containing the entire prion protein gene of a genetically diverse animal (e.g., a mouse containing a human prion protein gene) and an animal with its endogenous prion protein gene disrupted (e.g., a mouse with an ablated prion protein gene). Hybrids also specifically include crossing a transgenic animal having a chimeric prion protein gene with an animal with its endogenous prion protein gene ablated.

Dpl Transgenic Animals

The Dpl-encoding nucleic acids can be used to generate genetically modified non-human animals or site specific gene modifications in cell lines. The term "transgenic" is intended to encompass genetically modified animals having a deletion or other knock-out of Dpl gene activity, having an exogenous Dpl gene that is stably transmitted in the host cells, "knock-in" having altered Dpl gene expression, or having an exogenous Dpl promoter operably linked to a reporter gene. Of particular interest are homozygous and heterozygous knock-outs of Dpl.

Transgenic animals may be made through homologous recombination, where the Dpl locus is altered. Alternatively, a nucleic acid construct is randomly integrated into the genome. Vectors for stable integration include plasmids, retroviruses and other animal viruses, YACs, and the like. Of interest are transgenic mammals, preferably a mammal from a genus selected from the group consisting of Mus (e.g., mice), Rattus (e.g., rats), Oryctologus (e.g., rabbits) and Mesocricetus (e.g., hamsters). More preferably the animal is a mouse which is defective or contains some other alteration in Dpl gene expression or function.

A "knock-out" animal is genetically manipulated to substantially reduce, or eliminate endogenous Dpl function, preferably such that target gene expression is undetectable or insignificant. Different approaches may be used to achieve the "knock-out". A chromosomal deletion of all or part of the native Dpl homolog may be induced. Deletions of the non-coding regions, particularly the promoter region, 3' regulatory sequences, enhancers, or deletions of gene that activate expression of the Dpl genes. A functional knock-out may also be achieved by the introduction of an anti-sense construct that blocks expression of the native Dpl gene (for example, see Li et al., *Cell* 85:319–329 (1996)).

Conditional knock-outs of Dpl gene function can also be generated. Conditional knock-outs are transgenic animals that exhibit a defect in Dpl gene function upon exposure of the animal to a substance that promotes target gene alteration, introduction of an enzyme that promotes recombination at the target gene site (e.g., Cre in the Cre-loxP system), or other method for directing the target gene alteration.

For example, a transgenic animal having a conditional knock-out of Dpl gene function can be produced using the Cre-loxP recombination system (see, e.g., Kilby et al., *Trends Genet* 9:413–421 (1993)). Cre is an enzyme that excises the DNA between two recognition sequences, termed loxp. This system can be used in a variety of ways to create conditional knock-outs of Dpl. For example, two independent transgenic mice can be produced: one transgenic for a Dpl sequence flanked by loxp sites and a second transgenic for Cre. The Cre transgene can be under the control of an inducible or developmentally regulated promoter (Gu et al., *Cell* 73:1155–1164 (1993); Gu et al., *Science* 265:103–106 (1994)), or under control of a tissue-specific or cell type-specific promoter (e.g., a neuron-specific promoter or brain tissue-specific promoter). The Dpl transgenic is then crossed with the Cre transgenic to produce progeny deficient for the Dpl gene only in those cells that expressed Cre during development.

Transgenic animals may be made having an exogenous Dpl gene. For example, the transgenic animal may comprise a "knock-in" of a Dpl gene, such that the host cell genome contains an alteration that results in altered expression (e.g., increased (including ectopic) or decreased expression) of a Dpl gene, e.g., by introduction of an additional copy of the target gene, or by operatively inserting a regulatory sequence that provides for enhanced expression of an endogenous copy of the target gene. "Knock-in" transgenics can be transgenic animals having a heterozygous knock-in of the Dpl gene or a homozygous knock-in of the Dpl. "Knock-ins" also encompass conditional knock-ins.

The exogenous gene introduced into the host cell genome to produce a transgenic animal is usually either from a different species than the animal host, or is otherwise altered in its coding or non-coding sequence. The introduced gene may be a wild-type gene, naturally occurring polymorphism, or a genetically manipulated sequence, for example those previously described with deletions, substitutions or insertions in the coding or non-coding regions. The introduced sequence may encode a Dpl polypeptide, or may utilize the Dpl promoter operably linked to a reporter gene. Where the introduced gene is a coding sequence, it is usually operably linked to a promoter, which may be constitutive or inducible, and other regulatory sequences required for expression in the host animal.

Specific constructs of interest include, but are not limited to, anti-sense Dpl, or a ribozyme based on a Dpl sequence, which will block Dpl expression, as well as expression of dominant negative Dpl mutations, and over-expression of a Dpl gene. A detectable marker, such as lac Z may be introduced into the Dpl locus, where upregulation of expression of the corresponding Ngn gene will result in an easily detected change in phenotype. Constructs utilizing a promoter region of the Dpl genes in combination with a reporter gene or with the coding region of Dpl are also of interest. Constructs having a sequence encoding a truncated or altered (e.g, mutated) Dpl are also of interest.

The modified cells or animals are useful in the study of function and regulation of Dpl and other proteins involved the CNS and embryonic development. Such modified cells or animals are also useful in, for example, the study of the function and regulation of neurotoxic and/or neurodegenerative processes affected by Dpl, as well as the study of the prion family of genes in vivo. Thus, the transgenic animals of the invention are useful in identifying both downstream targets of Dpl and potentially a receptor for Dpl, as such may have a role in the phenotypes associated with defects in Dpl.

Animals may also be used in functional studies, drug screening, etc., e.g. to determine the effect of a candidate drug on embryonic development, neurodegeneration, or on symptoms associated with disease or conditions associated with Dpl defects (e.g., on symptoms associated with neurotoxicity. A series of small deletions and/or substitutions may be made in the Dpl genes to determine the role of different polypeptide-encoding regions in DNA binding, transcriptional regulation, etc. By providing expression of Dpl protein in cells in which it is otherwise not normally produced (e.g., ectopic expression), one can induce changes in cell behavior. These animals are also useful for exploring mechanistic models of neurodegeneration, and in particular the mechanisms involved in plaque formation, e.g. $PrP^{Sc}$ plaques in the brain.

DNA constructs for homologous recombination will comprise at least a portion of the Dpl gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al., *Methods in Enzymology* 185:527–537 (1990).

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene. Chimeric animals having the modification (normally chimeric males) are mated with wildtype animals to produce heterozygotes, and the heterozygotes mated to produce homozygotes. If the gene alterations cause lethality at some point in development, tissues or organs can be maintained as allogeneic or congenic grafts or transplants, or in in vitro culture.

Production of an overt morphological defect in single or double gene ablated mice may pave the way for precise assignment of Dpl and PrP$^C$ functions. The role of Dpl overexpression in Purkinje cell degeneration or alternatively, of closely linked genes present within extant Prn BAC and YAC clones (Westaway et al., *Proc. Natl. Acad. Sci. USA* 91, 6418–6422 (1994)) can be assessed by use of heterologous promoter elements. It will be of interest to test the susceptibility of mice, which overexpress Dpl or which harbor null or mutant alleles of PrnD to infection with prions.

Investigation of genetic function may also utilize non-mammalian models, particularly using those organisms that are biologically and genetically well-characterized, such as *C. elegans, D. melanogaster* and *S. cerevisiae*. For example, transposon (Tcl) insertions in the nematode homolog of a Dpl gene or a promoter region of a Dpl gene may be made. The Dpl gene sequences may be used to knock-out or to complement defined genetic lesions in order to determine the physiological and biochemical pathways involved in function of prion-like proteins. It is well known that human genes can complement mutations in lower eukaryotic models.

Production of Dpl Polypeptides

Dpl-encoding nucleic acid may be employed to synthesize full-length Dpl polypeptides or fragments thereof, particularly fragments corresponding to functional domains; DNA binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. In many situations, it may be desirable to express the Dpl genes in mammalian cells, especially where the encoded polypeptides will benefit from native folding and post-translational modifications. Small peptides can also be synthesized in the laboratory.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification technique. The purified polypeptide will generally be at least about 80% pure, preferably at least about 90% pure, and may be up to and including 100% pure. Pure is intended to mean free of other proteins, as well as cellular debris.

The Dpl polypeptides can be used for the production of antibodies, where short fragments provide for antibodies specific for the particular polypeptide, and larger fragments or the entire protein allow for the production of antibodies over the surface of the polypeptide. Antibodies may be raised to the wild-type or variant forms of Dpl, including forms of Dpl that may be associated with disease states or naturally occurring allelic variants. Antibodies may be raised to isolated peptides corresponding to these domains, or to the native protein, e.g by immunization with cells expressing Dpl, immunization with liposomes having Dpl polypeptides inserted in the membrane, etc.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

Isolation of Dpl Allelic Variants and Homologues in Other Species

Other mammalian Dpl genes can be identified and their function characterized using the Dpl genes used in the present invention. Dpl genes of interest include, but are not limited to, mammalian (e.g., human, rodent (e.g, murine, or rat), bovine, feline, canine, and the like) and non-mammalian (e.g., chicken, reptile, and the like). Methods for identifying, isolating, sequencing, and characterizing an unknown gene based upon its homology to a known gene sequence are well known in the art (see, e.g., Sambrook et al., *Molecular Cloning: A Laboratory Manual*, CSH Press 1989).

Drug Screening

The animal models of the invention, as well as methods using the Dpl polypeptides in vitro, can be used to identify candidate agents that affect Dpl expression (e.g., by affecting Dpl promoter function) or that interact with Dpl polypeptides. Agents of interest can include those that enhance, inhibit, regulate, or otherwise affect Dpl activity and/or expression. Agents that alter Dpl activity and/or expression can be used, for example: to treat or study disorders associated with increased Dpl activity (e.g., neurodegenerative disorders); to treat various degenerative or developmental conditions, e.g. inappropriate neural outgrowth or other conditions that are altered by a change in Dpl expression, activity, and/or conformation; and to facilitate development of $PrP^{Sc}$ either in vitro or in vivo. Candidate agents include synthetic molecules (e.g., small molecule drugs, peptides, or other synthetically produced molecules or compounds, as well as recombinantly produced gene products) as well as naturally-occurring compounds (e.g., polypeptides, endogenous factors, plant extracts, and the like).

Drug Screening Assays

Of particular interest in the present invention is the identification of agents that have activity in affecting Dpl expression and/or function. Such agents are candidates for development of treatments for, for example, increased and/or inappropriate neural outgrowth, or other condition that may be associated with altered Dpl activity. Drug screening identifies agents that provide a replacement or enhancement for Dpl function in affected cells. Conversely, agents that reverse or inhibit Dpl function may provide a means to regulate neurodegeneration or neurotoxicity, especially in Purkinje cells. Of particular interest are screening assays for agents that have a low toxicity for human cells.

The term "agent" as used herein describes any molecule, e.g. protein or pharmaceutical, with the capability of altering or mimicking the expression or physiological function of Dpl. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening of Candidate Agents In Vivo

Agents can be screened for their ability to affect Dpl expression or function or to mitigate an undesirable phenotype (e.g., a symptom) associated with an alteration in Dpl expression or function. In a preferred embodiment, screening of candidate agents is performed in vivo in a transgenic animal described herein. Transgenic animals suitable for use in screening assays include any transgenic animal having an alteration in Dpl expression, and can include transgenic animals having, for example, an exogenous and stably transmitted human Dpl gene sequence, a reporter gene composed of a (removed human) Dpl promoter sequence operably linked to a reporter gene (e.g., β-galactosidase, CAT, or other gene that can be easily assayed for expression), or a homozygous or heterozygous knockout of a Dpl gene. The transgenic animals can be either homozygous or heterozygous for the genetic alteration and, where a sequence is introduced into the animal's genome for expression, may contain multiple copies of the introduced sequence. Where the in vivo screening assay is to identify agents that affect the activity of the Dpl promoter, the Dpl promoter can be operably linked to a reporter gene (e.g., luciferase) and integrated into the non-human host animal's genome or integrated into the genome of a cultured mammalian cell line.

The candidate agent is administered to a non-human, transgenic animal having altered Dpl expression, and the effects of the candidate agent determined. The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent hat approaches an upper limit of the amount that can be delivered successfully to the animal), and may include delivery of the agent in different formulation. The agents can be administered singly or can be combined in combinations of two or more, especially where administration of a combination of agents may result in a synergistic effect.

The effect of agent administration upon the transgenic animal can be monitored by assessing Dpl function as appropriate (e.g., by examining expression of a reporter or fusion gene), or by assessing a phenotype associated with the Dpl expression. For example, where the transgenic animal used in the screen contains a defect in Dpl expression (e.g., due to a knock-out of the gene), the effect of the candidate agent can be assessed by determining levels of neurodegeneration in the control mouse relative to the levels produced in the Dpl defective transgenic mouse and/or in wildtype mice (e.g, by assessing levels of ataxia in the treated mice). Methods for assaying neurological defects in rodent are well known in the art. Where the in vivo screening assay is to identify agents that affect the activity of the Dpl promoter and the non-human transgenic animal (or cultured mammalian cell line) comprises a Dpl promoter operably linked to a reporter gene, the effects of candidate agents upon Dpl promoter activity can be screened by, for example, monitoring the expression from the Dpl promoter (through detection of the reporter gene) and correlation of altered Dpl promoter activity with neuronal activity and/or degeneration. Alternatively or in addition, Dpl promoter activity can be assessed by detection (qualitative or quantitative) of Dpl mRNA or protein levels. Where the candidate agent affects Dpl expression, and/or affects a Dpl-associated phenotype, in a desired manner, the candidate agent is identified as an agent suitable for use in therapy of a Dpl-associated disorder or a PrP-associated disorder.

Screening of Candidate Agents In Vitro

In addition to screening of agents in Dpl transgenic animals, a wide variety of in vitro assays may be used for this purpose, including labeled in vitro protein-protein binding assays, protein-DNA binding assays, electrophoretic mobility shift assays, immunoassays for protein binding, and the like. For example, by providing for the production of large amounts of Dpl protein, one can identify ligands or substrates that bind to, modulate or mimic the action of the proteins. The purified protein may also be used for determination of three-dimensional crystal structure, which can be used for modeling intermolecular interactions, transcriptional regulation, etc.

The screening assay can be a binding assay, wherein one or more of the molecules may be joined to a label, and the label diredtly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assays described herein. Where the assay is a binding assay, these include reagents like salts, neutral proteins, e.g. albumin, detergents, etc that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic Dpl function For example, candidate agents are added to a cell that lacks functional Dpl, and screened for the ability to reproduce Dpl activity in a functional assay. In a particular embodiment, agents that mimic unregulated Dpl activity are screened for the ability to decrease incubation time of prion disorders.

Many mammalian genes have homologs in yeast and lower animals. The study of such homologs' physiological role and interactions with other proteins in vivo or in vitro can facilitate understanding of biological function. In addition to model systems based on genetic complementation, yeast has been shown to be a powerful tool for studying protein-protein interactions through the two hybrid system described in Chien et al., *Proc. Natl. Acad. Sci. USA* 88:9578–9582 (1991). Two-hybrid system analysis is of particular interest for exploring transcriptional activation by Dpl proteins and to identify cDNAs encoding polypeptides that interact with Dpl. Binding to Dpl may influence the function/activity of particular target proteins or be itself functionally modulated and may bear relevance for both normal or specific disease states.

Identified Candidate Agents

The compounds having the desired pharmacological activity may be administered in a physiologically acceptable carrier to a host for treatment of a condition attributable or in part modulated by a defect in normal Dpl function (e.g., a neurological disorder associated with unregulated Dpl levels. The compounds may also be used to enhance Dpl finction. The therapeutic agents may be administered in a variety of ways, orally, topically, parenterally e.g. subcutaneously, intraperitoneally, by viral infection, intravascularly, etc. Inhaled treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing Agents, wetting and emulsifying Agents, salts for varying the osmotic pressure or buffers for securing an adequate pH value, and skin penetration enhancers can be used as auxiliary agents.

Pharmacogenetics

Pharmacogenetics is the linkage between an individual's genotype and that individual's ability to metabolize or react to a therapeutic agent. Differences in metabolism or target sensitivity can lead to severe toxicity or therapeutic failure by altering the relation between bioactive dose and blood concentration of the drug. In the past few years, numerous studies have established good relationships between polymorphisms in metabolic enzymes or drug targets, and both response and toxicity. These relationships can be used to individualize therapeutic dose administration.

Genotyping of polymorphic alleles is used to evaluate whether an individual will respond well to a particular therapeutic regimen. The polymorphic sequences are also used in drug screening assays, to determine the dose and specificity of a candidate therapeutic agent. A candidate Dpl polymorphism is screened with a target therapy to determine whether there is an influence on the effectiveness in treating, for example, a neurological disorder. Drug screening assays are performed as described above. Typically two or more different sequence polymorphisms are tested for response to a therapy.

Where a particular sequence polymorphism correlates with differential drug effectiveness, diagnostic screening may be performed. Diagnostic methods have been described in detail in a preceding section. The presence of a particular polymorphism is detected, and used to develop an effective therapeutic strategy for the affected individual.

Detection of Dpl Associated Disorders

Detection of Dpl levels and/or the presence of different conformations of Dpl can provide a means for diagnosing neurodegenerative disorders associated with Dpl. In particular, detection of changes in Dpl expression and/or changes in Dpl conformation may be associated with disorders involving Purkinje cell degeneration, such as hereditary cerebellar cortical atrophy, generalized epilepsy with tonic-clonic seizures (GTCS), spinocerebellar ataxia type 6, and the like. Measurement of Dpl levels and/or different conformations of the protein may also be used for other neurodegenerative disorders, as will be apparent to one skilled in the art upon reading the present disclosure.

Diagnosis of Dpl-associated disorders is performed by protein, DNA or RNA sequence and/or hybridization analysis of any convenient sample from a patient, e.g. biopsy material, blood sample, scrapings from cheek, etc. A nucleic acid sample from a patient having a disorder that may be associated with Dpl is analyzed for the presence of a predisposing polymorphism in Dpl. A typical patient genotype will have at least one predisposing mutation on at least one chromosome. The presence of a polymorphic Dpl sequence that affects the activity or expression of the gene product, and confers an increased susceptibility to a Dpl associated disorder (e.g, a neurodegenerative disorder) is considered a predisposing polymorphism. Individuals are screened by analyzing their DNA or mRNA for the presence of a predisposing polymorphism, as compared to sequence from an unaffected individual(s).

Screening may also be based on the functional or antigenic characteristics of the protein. Immunoassays designed to detect predisposing polymorphisms in Dpl proteins may be used in screening. Where many diverse mutations lead to a particular disease phenotype, functional protein assays can be effective screening tools.

Biochemical studies may be performed to determine whether a candidate sequence polymorphism in the Dpl coding region or control regions is associated with disease. For example, a change in the promoter or enhancer sequence that affects expression of Dpl may result in predisposition to neurological disorders, e.g. prion-mediated disorders. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like. The activity of the encoded Dpl protein may be determined by comparison with the wild-type protein.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. Cells that express Dpl genes may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al., *Science* 239:487 (1985); a review of current techniques may be found in Sambrook, et al., *Molecular Cloning: A Laboratory Manual*, CSH Press 1989, pp.14.2–14.33. Amplification may also be used to determine whether a polymorphism is present, by using a primer that is specific for the polymorphism. Alternatively, various methods are known in the art that utilize oligonucleotide ligation as a means of detecting polymorphisms, for examples see Riley et al., *Nucl. Acid Res.* 18:2887–2890 (1990); and Delahunty et al., *Am. J. Hum. Genet.* 58:1239–1246 (1996).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{33}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to either a neutral Dpl sequence (e.g., a Dpl sequence from an unaffected individual). Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

The hybridization pattern of a control and variant sequence to an array of oligonucleotide probes immobilized on a solid support, as described in U.S. Pat. No. 5,445,934, or in WO 95/35505, may be used as a means of detecting the presence of variant sequences. In one embodiment of the invention, an array of oligonucleotides are provided, where discrete positions on the array are complementary to at least a portion of mRNA or genomic DNA of the Dpl locus. Such an array may comprise a series of oligonucleotides, each of which can specifically hybridize to a nucleic acid sequence, e.g,. mRNA, cDNA, genomic DNA, etc. from the Dpl locus. Usually such an array will include at least 2 different polymorphic sequences, ie. polymorphisms located at unique positions within the locus, usually at least about 5, more usually at least about 10, and may include as many as 50 to 100 different polymorphisms. The oligonucleotide sequence on the array will usually be at least about 12 nt in length, may be the length of the provided polymorphic sequences, or may extend into the flanking regions to generate fragments of 100 to 200 nt in length. For examples of arrays, see Hacia et al., *Nature Genetics* 14:441–447 (1996); Lockhart et al., *Nature Biotechnol.* 14:1675–1680 (1996); and De Risi et al., *Nature Genetics* 14:457–460 (1996).

Antibodies specific for Dpl polymorphisms may be used in screening immunoassays. A reduction or increase in Dpl and/or presence of a Dpl disorder associated polymorphism is indicative that the suspected disorder is Dpl-associated. A sample is taken from a patient suspected of having a Dpl-associated disorder. Samples, as used herein, include tissue biopsies, biological fluids, organ or tissue culture derived fluids, and fluids extracted from physiological tissues, as well as derivatives and fractions of such fluids. The number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

Diagnosis may be performed by a number of methods. The different methods all determine the absence or presence or altered amounts of normal or abnormal Dpl in patient cells suspected of having a predisposing polymorphism in Dpl. For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

If the particular disease state is associated with conformational transition of Dpl, diagnosis may rely on the recognition of the disease-associated conformation of the protein. The disease-associated form the protein may be distinguished from other forms of Dpl using characteristics of the disease-associated conformation, e.g. insolubility, resistance to protease digestion, change in epitope availability and the like.

An alternative method for diagnosis depends on the in vitro detection of binding between antibodies and Dpl in a lysate. Measuring the concentration of Dpl binding in a sample or fraction thereof may be accomplished by a variety of specific assays. A conventional sandwich type assay may be used. For example, a sandwich assay may first attach Dpl-specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of normal and/ or abnormal Dpl is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second antibody is applied. The antibody will bind Dpl with sufficient specificity such that it can be distinguished from other components present. The second antibodies may be labeled to facilitate direct, or indirect quantification of binding. Examples of labels that permit direct measurement of second receptor binding include radiolabels, such as $^3$H or $^{125}$I, fluorescers, dyes, beads, chemiluminescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for Dpl as desired, conveniently using a labeling method as described for the sandwich assay.

Other diagnostic assays of interest are based on the functional properties of Dpl proteins. Such assays are particularly useful where a large number of different sequence changes lead to a common phenotype. For example, a functional assay may be based on the changes in the transcriptional repertoire of cells mediated by addition of mediated by Dpl gene products. Other assays may, for example, detect conformational changes, size changes resulting from insertions, deletions or truncations, or changes in the subcellular localization of Dpl proteins.

In a protein truncation test, PCR fragments amplified from the Dpl gene or its transcript are used as templates for in vivo transcription/translation reactions to generate protein products. Separation by gel electrophoresis is performed to determine whether the polymorphic gene encodes a truncated protein, where truncations may be associated with a loss of function.

Diagnostic screening may also be performed for polymorphisms that are genetically linked to a predisposition for prion-mediated disorders such as CJD, particularly through the use of microsatellite markers or single nucleotide polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al., *Genomics* 24:225–233 (1994); Ziegle et al., *Genomics* 14:1026–1031 (1992); Dib et al., supra.

Microsatellite loci that are useful in the subject methods have the general formula:

$$U(R)_n U',$$

where

U and U' are non-repetitive flanking sequences that uniquely identify the particular locus, R is a repeat motif, and n is the number of repeats. The repeat motif is at least 2 nucleotides in length, up to 7, usually 2–4 nucleotides in length. Repeats can be simple or complex. The flanking sequences U and U' uniquely identify the microsatellite locus within the human genome. U and U' are at least about 18 nucleotides in length, and may extend several hundred bases up to about 1 kb on either side of the repeat. Within U and U', sequences are selected for amplification primers. The exact composition of the primer sequences are not critical to the invention, but they must hybridize to the flanking sequences U and U', respectively, under stringent conditions. Criteria for selection of amplification primers are as previously discussed. To maximize the resolution of size differences at the locus, it is preferable to chose a primer sequence that is close to the repeat sequence, such that the total amplification product is between 100–500 nucleotides in length.

The number of repeats at a specific locus, n, is polymorphic in a population, thereby generating individual differences in the length of DNA that lies between the amplification primers. The number will vary from at least 1 repeat to as many as about 100 repeats or more.

The primers are used to amplify the region of genomic DNA that contains the repeats. Conveniently, a detectable label will be included in the amplification reaction, as previously described. Multiplex amplification may be performed in which several sets of primers are combined in the same reaction tube. This is particularly advantageous when limited amounts of sample DNA are available for analysis. Conveniently, each of the sets of primers is labeled with a different fluorochrome.

After amplification, the products are size fractionated. Fractionation may be performed by gel electrophoresis, particularly denaturing acrylamide or agarose gels. A convenient system uses denaturing polyacrylamide gels in combination with an automated DNA sequencer, see Hunkapillar et al., *Science* 254:59–74 (1991). The automated sequencer is particularly useful with multiplex amplification or pooled products of separate PCR reactions. Capillary electrophoresis may also be used for fractionation. A review of capillary electrophoresis may be found in Landers, et al., *Bio Techniques* 14:98–111 (1993). The size of the amplification product is proportional to the number of repeats (n) that are present at the locus specified by the primers. The size will be polymorphic in the population, and is therefore an allelic marker for that locus.

Diagnosis and Therapeutic Treatment of PrP-associated Disorders

Animals with increased expression of Dpl activity, such as the two $PrP^{0/0}$ lines described herein, also display a reduced incubation period for development of the symptoms of prion infection. Based on this observation, the present invention provides assay methods for determining the prion infectivity of a sample using animals that have an altered expression of Dpl. The method determines whether a sample is infected with prions by inoculating a Dpl transgenic or hybrid mammal of the invention with a sample to be tested and observing the mammal for a period of time sufficient to determine if they develop symptoms of a disease normally associated with prions. The animals may have an increased level of Dpl expression due to 1) a natural endogenous Dpl mutation, e.g. a mutation in the Dpl locus identified in a genetic screen; 2) a Dpl mutation produced in a transgenic animal, e.g. a deletion of the PrP locus that results in increased expression of the Dpl gene product; and/or 3) the introduction of an exogenous transgene that encodes a Dpl polypeptide.

The Dpl animals of the present invention can also be used in a method for determining the cause of death of an animal. Such a method involves inoculating a Dpl transgenic or hybrid animal of the invention with body fluid or tissue such as extracted brain tissue from the animal which has died (and preferably inoculating control animals with a standardized preparation of prions) and observing the transgenic or hybrid animal (and control animals) in order to determine if the animal develops symptoms of prion infections.

In a preferred embodiment, the animals of the invention with altered Dpl activity also have a genome that is altered with respect to the PrP locus. Exemplary animals include, but are not limited to: (1) animals with ablated endogenous PrP genes, as disclosed in U.S. Pat. No. 5,698,763; (2) animals with an ablated endogenous PrP gene and an exogenous PrP transgene from a genetically diverse animal, as disclosed in U.S. Pat. No. 5,792,901 and U.S. Ser. No. 08/935,363; and (3) animals with an ablated endogenous PrP gene and an inducible PrP transgene, as disclosed in U.S. Ser. No. 09/052,963.

Preferred host animals are mice and hamsters, with mice being most preferred in that there exists considerable knowledge on the production of transgenic animals. Other possible host animals include those belonging to a genus selected from Mus (e.g. mice), Rattus (e.g. rats), Oryctolagus (e.g rabbits), and Mesocricetus (e.g hamsters) and Cavia (e.g., guinea pigs). In general mammals with a normal full grown adult body weight of less than 1 kg which are easy to breed and maintain can be used. The host PrP gene can be changed to include codons from genetically diverse PrP genes from test animals belonging to a genus selected from Bos, Ovis, Sus and Homo. Preferably, a mouse host PrP gene is changed to include codons from a human, cow or sheep PrP gene, with cow being most preferred. Cows are preferred because an important object of the invention is to use the animal to test a statistically significant number of cows in a herd of cows to determine if the cows are infected with prions which cause BSE, known as "mad cow" disease.

The present invention also provides a method of testing the efficacy of a drug in the treatment of disease developed as a result of infection with prions comprising administering a drug to be tested to a transgenic or hybrid animal infected with prions (preferably a standardized prion preparation) and observing and/or testing the mammal to determine if the drug aids in treating or slowing the progress of the disease or its symptoms. Such methods are described in U.S. Pat. No. 5,792,901 and U.S. Ser. No. 08/935,363, which are both incorporated herein by reference for this purpose.

The present invention also provides a method for treating prion disease by administration of a compound that downregulates Dpl expression and/or decreases Dpl activity. Since increased Dpl activity is associated with a reduction in the incubation period for prion disease, and since PrP$^c$ can rescue the increased Dpl phenotype (suggesting they may either interact or compete in a pathway), decreasing Dpl activity can slow or halt the progression of prion disorder, for example by prevention of the degeneration of neurons in response to PrP$^{Sc}$.

Therapeutic Uses of Dpl-Encoding Nucleic Acid

Dpl-encoding nucleic acid can be introduced into a cell to accomplish transformation of the cell, preferably stable transformation. Introduction of the Dpl-encoding nucleic acid into the cell can be accomplished according to methods well known in the art (e.g., through use of electroporation, microinjection, lipofection infection with a recombinant (preferably replication-deficient) virus, and other means well known in the art). Preferably, the Dpl-encoding nucleic acid is operably linked to a promoter that facilitates a desired level of Dpl polypeptide expression (e.g., a promoter derived from CMV, SV40, adenovirus, or a tissue-specific or cell type-specific promoter). Transformed cells containing the Dpl-encoding nucleic acid can be selected and/or enriched via, for example, expression of a selectable marker gene present in the Dpl-encoding construct or that is present on a plasmid that is co-transfected with the Dpl-encoding construct. Typically selectable markers provide for resistance to antibiotics such as tetracycline, hygromycin, neomycin, and the like. Other markers can include thymidine kinase and the like.

The ability of the transformed cells to express the Dpl-encoding nucleic acid can be assessed by various methods known in the art. For example, Dpl expression can be examined by Northern blot to detect mRNA which hybridizes with a DNA probe derived from the relevant gene. Those cells that express the desired gene can be further isolated and expanded in in vitro culture using methods well known in the art. The host cells selected for transformation with Dpl-encoding DNA will vary with the purpose of the ex vivo therapy (e.g., Dpl peptide production), the site of implantation of the cells, and other factors that will vary with a variety of factors that will be appreciated by the ordinarily skilled artisan.

Methods for in vivo delivery of a nucleic acid of interest for expression in a target cell are known in the art. For example, in vivo methods of gene delivery normally employ either a biological means of introducing the DNA into the target cells (e.g., a virus containing the DNA of interest) or a mechanical means to introduce the DNA into the target cells (e.g., direct injection of DNA into the cells, liposome fusion, pneumatic injection using a "gene gun," and the like).

The amount of DNA and/or the number of infectious viral particles effective to infect the targeted tissue, transform a sufficient number of cells, and provide for production of a desired level of Dpl can be readily determined based upon such factors as the efficiency of the transformation in vitro and the susceptibility of the targeted cells to transformation. Generally, the amounts of DNA can be extrapolated from the amounts of DNA effective for delivery and expression of the desired gene in an animal model. For example, the amount of DNA for delivery in a human is roughly 100 times the amount of DNA effective in a rat.

Regardless of whether the Dpl-encoding DNA is introduced in vivo or ex vivo, the DNA (or cells expressing the DNA) can be administered in combination with other genes and other agents. In addition, Dpl-encoding DNA (or recombinant cells expressing Dpl DNA) can be used therapeutically for disorders associated with, for example, a decrease in Dpl production, but which are not associated with an alteration in Dpl function per se.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Identification of the Prnd Locus

Previous large-scale sequencing studies of phage and cosmid molecular clones encompassing human, sheep, and the "a" allele of the mouse PrP gene, $Prnp^{a}$, failed to reveal any evidence of additional coding regions, either immediately adjacent to PrP or within intronic sequences (Lee et al., *Genome Res.* 8:1022–1037(1998)). However, sequencing of the mouse $Prnp^{b}$ cosmid clone I/LnJ-4 (Westaway et al., *Neuron* 7:59–68 (1991)), which extends further in a 3' direction and analysis with the "XGrail 1.3c" program (Uberbacher et al, *ORNL/TM* 11741 (1991)) revealed a candidate coding region at nt 36119 to 36,751 (FIG. 1A).

Cosmids and YAC clones were propagated by standard procedures and have been described previously (D. Westaway, *Cell* 76:117–29 (1994)). A 129Sv/J BAC clone 321L17 was identified from a library kindly provided by Millenium Pharmaceuticals.

The predicted amino acid sequence of this ORF (FIG. 2) exhibits homology to mammalian, marsupial and avian PrP. We refer to the putative gene as Prnd (prion gene complex, downstream) and the protein product as "Dpl" (downstream, prion protein-like: German, "double")

Southern blot analyses indicated that the putative coding region of Prnd was a single-copy sequence in the mouse genome. To exclude the Prnd ORF as an idiosyncracy of I/LnJ mice, we sequenced the corresponding chromosomal region from a C57B6-derived YAC clone (Westaway et al., *Proc. Natl. Acad. Sci. USA* 91:6418–6422 (1994)) and a 129/SvJ BAC clone 321L17. Both revealed an identical ORF. Furthermore, related ORFs are present in rats and humans, with the human PrnD gene positioned 27 kb 3' to PRNP. These data indicate that PrnD genes will be found to be present in all mammals.

Example 2

Structure of the Prnd Locus

Prnd cDNAs were isolated to demonstrate the splicing of mRNAs transcribed from this region and to define appropriate coding exons. The complimentary approaches of cDNA library screening and rapid amplification of cDNA ends (RACE) were undertaken using wild type adult mouse brain cDNA as starting material.

RACE Cloning of PrnD RNAs For 5' RACE analysis, "Marathon" mouse brain cDNA (Clontech, Palo Alto, Calif.) was amplified with adapter primer AP1 and the Prnd anti-sense strand primer DW1 12, 5'-CGGTTGGTCCACGGCGACCCGAA-3' (SEQ ID NO:6) (0.2 µM), using a Perkin-Elmer 2400 thermocycler and "touchdown" PCR conditions of 94° C. 20 seconds, 5 cycles of 94° C., 5 sec and 72° C., 360 seconds; 5 cycles of 94° C., 5 seconds and 70° C. 360 seconds; and 30 cycloes of 94° C., 5 seconds and 68° C., 360 seconds. Taq polymerase was used in conjunction with "TaqStart" antibody (Clontech, Palo Alto, Calif.). Size-fractionated reaction products were resuspended in Tricine buffer and a second-round of PCR was performed using a nested primer set: AP2 universal primer and the Prnd primer ORFP-R2 (0.2 µM), 5'-GCAGATCTCTTTGATCAGCC-3' (SEQ ID NO:7) (94° C., 60 seconds, and 20 cycles of 94° C. 10 seconds, 57° C., 20 seconds, 72° C. 150 seconds. Subsequent to verification by hybridization to a kinase-labeled internal primer DW95 5'-CAGATCCACCGAAGCTCGGG-3', (SEQ ID NO:8) PCR reaction products were either sequenced directly or subsequent to cloning into the plasmid vector pCR2.1 TOPO (Invitrogen). A similar strategy was adopted for cloning of 3' RACE products, using the nested primers DW111, 5'-TGGTGACCAGCTGCGTCAACGCCA-3' (SEQ ID NO:9) and

DW192, 5'-TGGGAAGGCCCTGAGCGACAACCGTG-3' (SEQ ID NO:10).

RT-PCR of Prnd mRNAs

Total RNA was prepared by the acid-phenol method and polyA-selected on oligo dT-latex (Quiagen). First-strand cDNA synthesis was carried out using 100 ng of polyA+ RNA primed with oligo dT or random hexamer primers (as noted) and MuLV reverse transcriptase, as recommended by the manufacturer (Stratagene, La Jolla, Calif.). 2 ng aliquots of cDNA synthesis reactions incubated plus or minus reverse transcriptase were either amplified directly, or following concentration and de-salting by ultrafiltration. In the latter instance, a cDNA first-strand synthesis reaction of 40 ul (equivalent to 160 ng cDNA) was diluted with 450 ul water and introduced into a 50,000 molecular weight cut-off "Eluticon" microconcentrator (Owl Scientific). Subsequent to spinning at 14,000×g, the membrane was washed with 500 ul water, spun, inverted and eluted with 10 ul water. 2.5 ul of this preparation was used per PCR reaction. Alternatively, 10 ug of total RNA was reverse-transcribed in a total volume of 50 ul using Superscript reverse transcriptase (Life Technologies) with 2.5 ul used per amplification reaction. "Hot-start" amplification (Platinum Taq", Life Technologies or Advantage KlenTaq, Clontech) was performed in standard reaction buffers, as noted below. Primer sets were as follows:

Prnd exon 1a to PrnD exon 2:

DW189=5'-GCTCCAAGCTTCAGAGGCCACAGTAGCA-3' (SEQ ID NO:11) and

DW96, 5'-TTACTTCACAATGAACCAAACGAAAC-3' (SEQ ID NO:12) (1 uM):

94° C., 180 seconds; 40 cycles of 94° C., 15 seconds; 65° C. 30 seconds; 72° C., 75 seconds, using Platinum Taq polymerase and MgCl$_2$ at a final concentration of 2 mM.

Intergenic exon 2 to PrnD exon 2: DW117, 5'-GAGTGGAGGTCTTCGCGCA-3' (SEQ ID NO:13) and DW96 (0.5 uM). 95° C. 300 seconds, and 45 cycles of 95° C., 10 seconds, 55° C. 20 seconds, 72° C. 150 seconds, using Platinum Taq polymerase, and MgCl$_2$ at a final concentrations of 2.5 mM.

Prnp exon 2 to PrnD exon 2:

5'UT.3 (Westaway, Neuron 7:59–68 (1991)) and DW96 (0.2 uM).

95° C. 300 seconds, and 40 cycles of 94° C., 15 seconds, 60° C. 30 seconds, 72° C. 120 seconds, using Platinum Taq polymerase and MgCl$_2$ and DMSO at a final concentrations of 2.5 mM and 4% respectively.

Rat Prnp exon 2 to the 3' end of PrnD (defined by ESTAI136375):

DW213 5'-TCA<u>A</u>AACTGAACCATTTCAACC<u>C</u>A<u>A</u>CTGAAG<u>T</u>ATTCTGCC-3' (SEQ ID NO:14) and DW214 5'-A<u>C</u>CCAG<u>C</u>GT<u>T</u>CTGGCCC<u>G</u>GTATTAGGATT-3' (SEQ ID NO:15) (mismatches to the mouse gene sequences are underlined). 94° C. for 120 seconds followed by 40 cycles of 94° C., 15 seconds, and 72° C. 240 seconds. β-Actin: these were used as recommended by the manufacturer (Statagene, La Jolla, Calif.).

Results from the RACE and RT-PCR analyses were used to search for EST matches from public databases and a number were retrieved from mouse, human and rat (FIG. 1B). PrnD cDNAs of 1.5 and 1.7 Kb were retrieved from a Balb/C testis cDNA library. These clones corresponded to the major Dpl mRNA species observed on Northern blots. A larger transcript of 2.7 Kb was also apparent on northern blots and 3' RACE provided good evidence for alternative splicing of exon 2, which could account for this MRNA species.

Examination of the two major cDNA clones indicated that they were nearly full length, as they contained polyA tracts at the 3' end and partial sequence from alternately spliced 5' exons. 5' RACE analysis was in close agreement with the sequence of these clones indicating splicing events from short 5' exons, denoted exons 1a and 1b respectively, starting at either nt 34,124 or nt 34,277 to a common splice acceptor lying immediately 5' to exon 2, the Prnd ORF, at nt 36,204 (FIG. 1B, FIGS. 2A, 2B). This was also in agreement with the sequence of a mouse Dpl EST AA796652, which is generated by splicing of exon 1b to exon 2 (FIG. 1B).

The 5' boundary of the PrnD 5' untranslated region exon was located within an interval of approximately 30 nucleotides by RT-PCR reactions with different primers (FIG. 2A). Primer extension reactions and nuclease protection assays were employed for more precise mapping. Primer-extension reactions with primers DW197, (5'-CCAGCCGGTTCTTCATGGTGAATCTCGG-3', (SEQ ID NO:16) hybridization temperature 65° C.), and DW123a, (5'-CATGGTGAATCTCGGTTCTC-3', (SEQ ID NO:17) hybridization temperature 55° C.), were carried-out as before (Westaway et al., 1987) except that primers were labeled to a specific activity of Æ 9×10$^7$ dpm/pmole using 6000 Ci/mmol gamma $^{32}$P-ATP ("Kinase Max", Ambion Inc: NEN). A 42-mer oligonucleotide labeled in the same manner was used for a nuclease protection assay ("Multi-NPA", Ambion Inc.).

Results of these mapping experiments were in close agreement, defining a cluster of mRNA start-sites 13–18 nucleotides upstream of 5' termini defined by RACE cDNAs and EST gbAA796652 (from mouse mammary gland). These assignments are also in accord with the structure of human Prnd cDNAs. Because of the alternative 3' boundaries of this 5' non-coding exon, arising from the use of two alternative splice donors, it is denoted "exon 1a/1b". Notably, a similar arrangement has been observed in the bovine PrP gene (Horuichi et al., Biochem. Biophys. Res.

Commun. 233:660–654 (1997)). Since neither exon 1a or 1b contains ATG codons in-frame with the chromosomal ORF, these cDNAs (and others described below) indicate that the initiation codon for Prnd lies 3' to the splice acceptor at nucleotide 36,212. This ATG is conserved and conforms closely to the Kozak consensus for the initiation of eukaryotic mRNAs (consensus GCCGCCa/gCCATGG; (SEQ ID NOS. 18,19) PrnD AGATTCACCATGA) (SEQ ID NO:20) (Kozak, *Nucleic Acids Res.* 15:8125–8148 1987). The position of the PrnD start site is organized in a similar fashion to Prn-p itself, where the ATG codon lies 10 nucleotides 3' to the splice acceptor of exon 3 (Westaway et al., *Cell* 51:651–662 (1987)).

The internal structures of independently-derived cDNAs indicated that the Prnd mRNA 3'UTR is encoded within separate exons and subject to alternative splicing (FIG. 1B). Thus one splice donor 28 nucleotides 3' of the ORF termination codon (position 36,779) codon and another further downstream at 37,472 supply a splice acceptor at position ~38,006, suggesting an explanation for the ~1.7 and 2.7 kb RNAs detected by Northern blots (below). cDNA clones containing polyA tracts were found to terminate at positions 39,099 and 39,315 in the I/LnJ-4 cosmid. While the more 3' site is preceded by a consensus polyadenylation signal, AATAAA, a similar motif is lacking from the 5' site. Of note, a sequence CTTAAA is located 27 nucleotides 5' of the polyA tail. This 3' gene architecture is unusual as (i) introns within 3'UTR coding sequences are rare, (ii) splice sites at positions 37,472 and 38,006 differ from the accepted consensus (such that definitive positioning of the exact intron boundaries are complicated by nucleotide redundancies whereby the boundary may be shifted by +1 or +2 from these coordinates) or a strain polymorphism, and (iii), intron 2 defines the putative protein coding exon of Prnd as being an internal, rather than a terminal exon, as in the case of Prnp. With a size of either 575 or 1,268 nucleotides (depending upon the selection of splice donor site) this exon contravenes the rule that 99% of internal exons are less than 400 bases in length (Berget, *J. Biol. Chem.* 270:2411–2414 (1995)).

Example 3

Expression of Transcripts From the Prnd Locus

Northern blot analyses were performed using the entire 570 bp PrnD ORF fragment derived from the ILn/J-4 cosmid using total (50 g loading) or oligo-dT selected RNA (7 g loading). Total RNA was made using Trizol reagent (Gibco) following the manufacturers instructions. Poly A+ RNA was isolated using a Oligotex mRNA kit (Qiagen). RNA samples were heated for 30 minutes to 50 deg C. in glyoxal sample buffer and electrophoresed on 1.2% agarose gels as recommended by the manufacturer (Ambion Inc., Woodland, Tex). RNA was transferred onto Hybond N+ (Amersham) in 5×SSC 10 mM NaOH for 2 hours using a turboblotter (Schleicher and Schuell), rinsed in 5×SSC, UV fixed (Statagene, La Jolla, Calif.) then prehybridized (6×SSC, 1% SDS, 3% (w/v) dextran sulfate, 10 ug/ml sonicated herring sperm DNA) for 1 hour at 65° C. prior to the addition of a 540bp Dpl ORF PCR a-dCTP$^{32}$ random-primed probe (Feinberg et al., *Anal. Biochem.* 132:6–13 (1983)) generated with the primers RM1 (5'-ATGAAGAACCGGCTGGGTAC-3') (SEQ ID NO:21) and DW96 with 129Sv/J genomic DNA template. Membranes were hybridized for 16 hours then rinsed for 5 minutes at room temperature in 2×SSC/1% (w/v) SDS, washed 30 minutes at 65 deg C. in 2×SSC/1% (w/v) SDS then 30 mins in 1×SSC/1% (w/v) SDS at 65 deg C. Blots were exposed at −80 deg C. for 3 days. This revealed Prnd mRNAs of approximately 1.7 and 2.7 kb in testis and heart polyA+ RNA of wild type mice. No Prnd mRNA was detected in brain.

Using RT-PCR, mRNA in wild type mice produced by splicing from exon 1a to exon 2 could be detected in adult brain cDNA and 14-day embryos (FIG. 3). Additional cDNA species, one of which reflects inclusion of exon 1b, were detected in some adult brain samples. Some preliminary evidence of Dpl mRNA expression can be derived from the tissue origin of the Prnd EST matches (FIG. 1B): mouse ESTs AA796652, AA104098 and AA190150 were derived from adult mammary gland, embryonic heart and adult spleen respectively. In sum, Prnd mRNAs are expressed in embryos, in peripheral tissues, and at low levels in the adult CNS.

As predicted from the DNA sequence data, species of similar electrophoretic mobility were apparent in brain RNA of Tg(MoPrP-B)2091 mice, harboring a high copy-number array of an ILn/J-4 cosmid transgene within which Dpl was first noted. A corresponding product was undetectable in wt control mouse brain samples as noted above.

Example 4

Computer Analysis of Dpl Sequences

Various non-redundant combinations of the SWISSPROT and TREMBL (A. Bairoch et al., *Nucleic Acids Res.* 19 Suppl:2247–9 (1991); Stoesser, et al., *Biochemistry* 37:7185–7193. (1998)) sequence databases were searched with the sequences of human and mouse Dpl using the alignment programs FASTA_3 (Pearson et al., *Proc. Natl. Acad. Sci. USA* 85:2444–2448 (1988)) and PSI_BLAST (S. F. Altschul et al., *Nucleic Acids Res.*25:3389–402 (1997). The Dpl proteins show distant but significant homology (24–26% identity over ~160 residues) to many PrP sequences (FASTA_3 score E( )=0.00015, where E( ) is the expected number of sequence matches by chance; PSI-BLAST E( )=2×10(−41) for alignment with domestic dog PrP).

Possible transmembrane segments were predicted using TopPred 2 (G. von Heijne, *J Mol Biol.* 225:487–94 (1992)) and TMPred (See e.g. D. S. Millican et al., *Endocr Res.* 24:387–90 (1998). N-terminal signal peptide cleavage sites for human and MoDop were predicted to be at the positions indicated using the SignalP program (H. Nielsen, *Int J Neural Syst.* 8:581–99 (1997)). This program locates eukaryotic signal peptides with ~70% accuracy. However, 50% of Type-II N-terminal transmembrane segments are over-predicted as signal peptides. The GPI attachment site (denoted w) and the succeeding two residue positions (w+1 and w+2) have distinct residue preferences and aversions, e.g. preferences for serine and aspartic acid at position w (Y. Furukawa *Biochim Biophys Acta* 1328:185–96 (1997); P. Harrison, unpublished data) and requires a stretch of mostly hydrophobic residues (8–31 residues long) in the cleaved C-terminal signal peptide. This region is separated from w+2 by a 2–8 residue segment of greater hydrophilicity. Both signals are found in the Dpl sequences. The most likely GPI-anchor attachment site for Dpl ({w, w+1, w+2}= G155A(G or A)) was determined from an examination of the literature on GPI anchors, the sequence homology between the Dpls and PrPs at the C-terminus and from a representative set of GPI-anchored proteins culled from sequence databases (P. Harrison, unpublished data) (FIGS. 2 and 5. The GPI anchor site suggested by the multiple sequence alignment ({w, w+1, w+2}=G157LR) is unlikely (FIG. 2) as w+1 is almost never a large aliphatic hydrophobic or aromatic (97%; 61/63 examples) and w+2 is almost never charged (or large aliphatic hydrophobic or aromatic) (98%; 62/63) (P. Harrison, unpublished data). Other possible attachment sites in this region can be discounted for similar reasons, leaving only the suggested site, {w, w+1, w+2}= G155A(G or A).

Example 5

Chimeric Prnp/PrnD mRNAs

In parallel to RACE and cDNA cloning, the gene-finding program "GRAIL" was also used to identify possible 5' exons of PrnD. Analyses of the relevant area of the I/LnJ-4 cosmid sequence did not detect exon 1a/1b, but instead two putative sense-strand exons (nt 29,589–29,672; "Grail exon 6" and nt 29,798–29,832; "Grail exon 7") between the Prnp and PrnD ORFs. Using a primer located in "grail exon 6", cDNA could be amplified from adult wild-type mouse brain RNA, with DNA sequencing confirming splicing from a consensus splice donor at nucleotide 29,671 to the PrnD exon 2 splice acceptor (FIG. 4).

These RT-PCR analyses defined grail exon 6 as a new 5' exon (FIG. 4, intergene exon 2), but our failure to identify cDNAs including PrnD exon 1a/1b (or "Grail exon 7") suggested that conserved sequences 5' to exon 1a constitute the PrnD promote proper. The possibility that the PrnD mRNAs including "Grail exon 6" originate from a more 5' promoter was then examined. Since the Prnp promoter is located only 23 Kb away and positioned in the correct transcriptional orientation, this was a strong candidate for the PrnD promoter as well. Using a 5' primer located in the Prnp exon 2 and a 3' primer in PrnD exon 2, a product was obtained in RT-PCR analyses of brain cDNA from wild-type mice (FIG. 4). Sequence analysis of these cDNAs confirmed their chimeric nature, that is, starting within the Prnp transcription unit at exon 2 and finishing within the PrnD transcription unit commencing at exon 2a (FIG. 5). Some cDNAs included the "Grail 6" exon interposed between Prnp exon 2 and PrnD exon 2a and thereby defined the 5' boundary of this exon as a consensus splice acceptor site at nucleotide 29,671. Other cDNAs included an additional exon (intergene exon 2), located between nucleotides 25,482 and 26004, in a sub-set of cDNAs. Alternative use of these two intergene exons results in a variety of chimeric mRNAs (FIG. 5).

Since there is only one precedent for intergenic splicing in the chromosomal genes of a higher mammal (Magrangeas et al., *J. Biol. Chem.* 273:16005–16010 (1998)), we sought to confirm our observations in a second species. Using the sequence of rat Prnp exon 2 and EST A1136375 homologous to the 3' boundary of mouse PrnD exon 3, RT-PCR experiments were performed for rat tissues.

As predicted, analogous chimeric cDNAs including two permutations of intergene exons were detected in both brain and testis. Since the two intergene exons are poorly conserved between mouse and rat (not presented) and fail to exhibit ATG codons in-frame with the PrnD ORF, we infer that they do not serve a protein coding function.

Example 6

Establishment of Cell Lines Expressing Dpl

In order to better study the activity and/or cellular interactions of Dpl, a Dpl transgene was transfected into an established neuronal cell line.

Preparation of Mammalian Dpl-expression Vector

A PrnD cDNA cassette was prepared by amplification of the B6-9 YAC clone with the oligonucleotide primer pair DW174=5'-CGGAATTCCAGCCTTTCCCTTGCCGATTCAC-3' and

DW175=5'-GCTCTAGAACTGGGCTACCTCTGTCTACCT-3'.

The 5' primer of this pair alters the exon 2a splice acceptor site. Subsequent to digestion with EcoR1 and Xba the resulting cDNA cassette was gel-purified and cloned into the mammalian expression vector pcDNA3.0 (Invitrogen).

Establishment of Stable Dpl Cell Lines pcDNA3.0_Dpl (1–5 g) was added to 0.1 mL Opti-MEM (Life Technologies), mixed with 15 L LipofectAMINE reagent (Life Technologies) and then incubated at room temperature for 40 minutes. Neuro-2a cells [N2a] (ATCC), cultured in high glucose DMEM (Life Technologies) supplemented with 10% fetal bovine serum [FB S] (Life Technologies), were grown to 60% confluency in 6 cm dishes. Cells were washed twice with Hank's balanced salt solution [HBBS] and 2 mL Opti-MEM was added to each dish. The lipid/DNA mixture was added dropwise to each dish with gentle mixing and cells were incubated for 5 hours at 37° C. Cells were also transfected with pcDNA3.0 lacking the Prns insert, and Opti- MEM/lipid mixture containing no DNA as negative controls. Cells were then fed with 1 mL DMEM containing 20% FBS and incubated overnight at 37° C. Trypsinized cells and seeded 10 cm plates with DMEM containing 10% FBS and 1 mg/mL G418. Individual colonies were selected and expanded after 2 weeks of selection, and maintained in DMEM containing 10% FBS and 0.3 mg/mL G418.

Preparation of RNA From Cell Lines

Cells were grown to ~80% confluency in 75 cm flasks, washed three times in 12 mL HBBS. Cells were scraped into 5mL ice-cold HBBS and pelleted at 1,000×g for 5 min at 4° C. Cells were resuspended in 1 mL ice-cold HBBBS, transferred to a RNA-free microfuge tube (Ambion) and pelleted at 14,000 rpm for 1 minute at 4° C. The pellet was resuspended in 0.6 mL freshly-prepared denaturing solution (4M guanidinium thiosulphate, 25 mM sodium citrate, pH 7.0, 0.5% Sarkosyl, 0.1M β-mercaptoethanol). Next 60 L 2M sodium acetate, pH4.0, 0.6 mL acid phenol, and 0.13 mL chloroform: isoamyl alcohol (24:1) were added and the contents of the tube were mixed vigorously by shaking. The sample was incubated on ice of 20 min and then spun at 14,000 rpm for 20 minutes at 4° C. The aqueous phase was transferred to a new RNA-free microfuge tube and 0.6 mL ice-cold isopropanol was added. The tube was mixed by shaking and incubated at −20° C. for 1 hr. The tube was then centrifuged at 14,000 rpm at 4° C. for 20 min and the isopropanol was removed. The pellet was washed in 75% ethanol, made up using DEPC-treated ddH$_2$O, and incubated at −20° C. for 20 min. The tube was then spun at 14,000 rpm at 4° C. for 20 min and the ethanol was removed. After air-drying, the pellet was resuspended in 30 L DEPC-ddH$_2$O, 1 L was in order to determine the RNA concentration by absorbence at 260 nm, and the sample was immediately snap frozen on dry-ice and stored at −80° C.

Northern Blot Analysis of Dpl Cell Lines

RNA samples were thawed on ice and brought to 2 g/L using DEPC-ddH$_2$O. 5 L of each sample was analyzed. Total RNA was fractionated on a 1% agarose gel containing formaldehyde using the NorthernMax kit (Ambion). The gel was then transferred to Nytran-plus membrane (S&S) also using the NorthernMax kit. A 400 bp Dpl ORF fragment was prepared by PCR amplification of the PrnD cDNA cassette using primers DW95 and DW96, and random primed using the DECAprime II kit (Ambion). The membrane was hybridized using ExpressHyb solution (Clontech) and exposed to X-ray film at −80° C. for 72 hr.

Example 7

Dpl regulation and Ataxic Behavior in $Prnp^{0/0}$ Mice

The alteration of Prnd expression in $Prnp^{0/0}$ lines was determined to be responsible for the ataxia observed in two PrP knockout lines of mice lines (Sakaguchi et al., *Nature* 380:528–531 (1996)). cDNAs prepared from different lines of $Prnp^{0/0}$ mice were shown to behave differently in semi-quantitative RT-PCR analyses. The differences corresponded with both the structure of the ablated allele design and the PrP deficient phenotype. The structures of the 4 independently generated alleles is shown in FIG. 6, and fit into two main classes: those that create in internal insertion/deletion within PrP exon 3 (Büeler et al., *Nature* 356:577–582 (1992); Manson et al., *Mol. Neurobiol.* 8:121–127 (1994)), which do not develop a late-onset ataxia, and two alleles which remove the entire PrP ORF but also a ~1 Kb region 5' to exon 3, including the exon 3 splice acceptor site. Thus Zrch $Prnp^{0/0}$ mice (Büeler et al., *Nature* 356:577–582 (1992)) with an intact splice acceptor gave no signal while the Rcm and Ngsk lines of $Prnp^{0/0}$ mice with an ablated exon 3 splice acceptor site showed a potent increase in chimeric mRNA relative to wild-type mice. Control PCR reactions performed with alternative primer sets were used to exclude trivial differences between cDNA preparations.

Northern blot analyses showed that the expression levels of Dpl mRNA in brain increases dramatically in the two $Prnp^{0/0}$ lines developing ataxia. Thus, overexpression of PrnD mRNA in brain is associated with the development of ataxia in Ngsk and Rcm $Prnp^{0/0}$ mice while the low levels of PrnD mRNA in brains of Zrch $Prnp^{0/0}$ mice is not accompanied by cerebellar dysfunction. The following table summarizes these results:

TABLE 1

Cerebellar ataxia and Dpl expression in lines of $Prnp^{\%}$ mice

| $Prnp^{\%}$ line | Ataxia and cerebellar degeneration in aged mice | Deletion of exon 3 splice acceptor in Prnp null allele | Overexpression of PrnD mRNA in brain |
|---|---|---|---|
| Zrch | absent | no | no |
| Npu | absent | no | ND |
| Ngsk | present | yes | yes |

Profound overexpression of Prnd occurs in Ngsk and Rcm lines of $Prnp^{0/0}$ mice, both of which develop ataxia. Equally striking is the finding that Purkinje cells remain healthy in Zrch $Prnp^{0/0}$ mice, which do not overexpress Prnd. These findings suggest that overexpression of Prnd toxic for Purkinje cells. Because expression of chimeric mRNAs is dependent upon the Prnp promoter, it is of interest to note that this promoter is active in Purkinje cells (Nishida et al., in press), with a putative Purkinje cell-specific enhancer element inferred to exist either within Prnp intron 2 or 3' of a Sal I restriction site in the Prnp/Prnd intergene region (Fischer et al., *EMBO J.* 15:1255–1264 (1996)).

Example 8

Predicted Features of the Dpl Proteins

Comparison of available Dpl peptide sequences reveals a protein which is highly conserved, providing evidence that Dpl is a functional gene product under selection pressure (FIGS. 7 and 8). Mouse and rat Dpl proteins share >90% identity whilst mouse with the human Dpl ORF reveals 76% sequence identity. The majority of the sequence differences between mouse and human (94%, 32/34) are conservative amino acid replacements. Homology between Dpls and mouse PrP are estimated at between 20 and 24%, slightly lower than that observed between chicken and mammalian PrPs (31–34%) (Gabriel et al., Molecular cloning and structural analysis of a candidate chicken prion protein. In Prion Diseases of Humans and Animals, S. B. Prusiner, J. Collinge, J. Powell and B. Anderton, eds. (London: Ellis Horwood), pp.407–431 (1992); Harris et al., *Proc. Nat. Acad. Sci USA* 88:7664–7668 (1991)). Dpls from all three species have a predicted N-terminal signal peptide cleavage site indicating that they are synthesized, like $PrP^C$, in the secretory pathway (FIG. 9). PrP has a cluster of basic residues rich in arginine and lysine adjacent to a predicted N-terminal signal peptide cleavage site and Dpl shares a similar feature between residues 25 to 38 in which 7 residues (50%) are basic.

Dpl lacks a convincing His/Pro/Gly rich octarepeat region which is present in PrP and which is thought to bind Cu(II) ions in vivo (Brown et al., *Nature* 390:684–687 (1997); Stöckel et al., *Biochemistry* 37:7185–7193 (1998); Viles et al., *Proc. Natl. Acad. Sci. USA* 96:2042–2047). However, mouse Dpl has a short PSSGGQ motif between codons 41–46 very similar to a PSSGGS motif in chicken PrP codons 103–108. The significance of this observation is uncertain because we are unsure whether Dpl or PrP is the original molecule: i.e. whether Dpl was generated from a recent gene duplication of PrP or vice versa. Either way, it could be argued that this motif represents a vestigial repeat which has been deleted or, alternately, a prototypic unit which has been amplified to form the repeat structure within PrP.

Dpl lacks a region with significant homology to the AGAAAAGA motif completely conserved in all known PrP sequences and corresponding to mouse PrP codons 112–119 (Bamborough et al., *Cold Spring Harb. Symp. Quant. Biol.* 61:495–509 (1996); Schatzl et al., *J. Mol. Biol.* 245:362–374 (1995)). This difference may indicate a significant functional divergence between Dpl and PrP because this region of PrP has been shown to be critical for PrP topology in the ER membrane (Hegde et al., *Science* 279:827–834 (1998)) and the synthetic PrP peptide 106–126 has also been shown to be neurotoxic to primary cultures exposed to the synthetic peptide 106–126 (Forloni et al., *Nature* 362:543–546 (1993)).

PrP has a glycosylphosphatidylinositol (GPI) anchor attached at its C-terminus at serine 231 (Stahl et al., *Cell* 51:229–240 (1987)). In common with PrP, Dpl has a hydrophobic C-terminal region and we predict that this may be compatible with either addition of a GPI anchor, or a single transmembrane domain. Although Dpl lacks a serine residue corresponding to the hamster PrP codon 231 we predict that a GPI may be attached at glycine 155. GPI attachment at a glycine has been demonstrated for the α-folate receptor (W. Yan and M. Ratnam, *Biochemistry* 34:14594–600 (1995). It is interesting to note here that examination of rabbit PrP sequence indicates that it has no serine at residue 231 suggesting that either rabbit PrP is not GPI anchored or that it and may by GPI anchored by a glycine residue rather than a serine.

Conservation of residues on the surface of two evolutionarily related proteins is also a useful indicator of functionally important elements (Lichtarge et al., *J. Molec. Biol.* 257:342–358 (1996)). PrP has two consensus N-linked glycosylation sites of the form N-x-(S or T). The N-linked glycosylation site analogous to N181 on helix B in MoPrP is maintained in Dpl but the site on helix C is lost (FIGS. 8 and 9). That this is the only conserved exposed residue on helix B argues for some functional significance of this complex-type glycosylation. An additional conserved consensus N-linked glycosylation site is found 13 residues amino terminal of this position (MoDop N-72: NVT) in an exposed surface loop. A minority of N-glycosylated proteins (~23%) have one or more unglycosylated consensus sites and only ~10% of consensus sites in N-glycosylated proteins are unglycosylated (G. von Heijne, *J Mol Biol.* 225:487–94 (1992)) indicating that this site is also likely to be glycosylated.

Electrostatic surface potential, evaluated using the GRASP algorithm (Nicholls et al., *Proteins* 11:281–296 (1991)), is distinct for Dpl and PrP. PrP has positively and negatively charged patches on opposing faces of the molecule (R. Riek, *Nature* 382:180–2), suggesting an orientation for membrane binding. Dpl maintains the positively charged patch seen in PrP although the boundaries of these areas are not equivalent but lacks a similar negatively charged patch (data not shown), having instead a neutral/positively-charged area. In general, the surface of Dpl has more positive charge in areas which, in the case of PrP, are thought not to be conformationally heterogeneous (i.e., residues 121–231). It seems likely that this disposition of charged surfaces might play a role in multimerization if are found to interact. Whether Dpl and PrP compete for binding to a common receptor remains to be established.

Since PrnD mRNAs are expressed at low levels in the CNS of wild-type animals, we sought evidence for Dpl protein in transfected cells expressing PrnD cDNAs under the control of a constitutive cytomegalovirus promoter. Untransfected N2A cells and stably transfected lines containing the CMV/Dpl plasmid and grown in the presence of selectable marker were harvested for RNA, which was assessed by Northern blot analysis. Whereas 1.7 and 2.8 kb PrnD mRNAs were detected in a positive control (testis RNA), they were undetectable in untransfected N2A cells. Of 8 stable transfected lines, 5 displayed abundant levels of the anticipated 0.9 kb MRNA derived from the expression plasmid.

Example 9

Detection of Dpl by Western Blot

Two clones with abundant MRNA were selected for further analysis by western blotting, using an antiserum directed against the Dpl-2 synthetic peptide. A 15 residue Dpl peptide 2 (NH-CFGAEGNRYYAANYY-COOH) (SEQ ID NO:5) corresponding to residues 71 to 84 was synthesized by FMOC chemistry and conjugated to maleimide activated KLH via a free sulfhydryl group. The conjugated peptide was mixed with RIBI prior to subcutaneous inoculation of rabbits.

Cells were grown to approximately 80% confluency in 10 cm dishes and washed three times with 10 mL HBBS. Cells were then scraped into 5 mL HBBS and pelleted at 1,000×g for 5 min at 4° C. The pellet was resuspended in 0.1 mL cell lysis buffer (20 mM Tris-HCl, pH8.0, 150 mM NaCl, 0.5% Triton X-100, 0.5% sodium deoxycholate, 1 Complete mini protease inhibitor tablet (Boehringer Mannheim)), transferred to a sterile microfuge tube and agitated at 4° C. for 10 minutes. Samples were pelleted at 14,000 rpm at 4° C. for 10 minutes and supernatant was transferred to a clean microfuge tube. Protein concentration was determined by Bradford assay as recommended by the manufacturer (Bio-Rad). Samples were brought up in 4× Laemmli buffer and stored at −80° C.

Both lines exhibited an intense heterodisperse signal with an apparent $M_r$ of 30–36 KDa. A comparable signal was absent from untransfected cells and clones not expressing PrnD mRNA. Normalized gel-loadings were confirmed by probing with an anti-actin antiserum. Since the predicted size of the full-length and N- and C-terminally processed Dpl is 20.4 and 14.9 KDa, respectively, we infer that Dpl is heavily glycosylated. This conclusion is in accord with the presence of two consensus sites for N-linked glycosylation sites and offers a strong parallel to the case of $PrP^c$ itself, where a 20 KDa polypeptide chain is increased in size to 33–35 KDa by the addition of carbohydrate chains.

Example 10

Rescue of Dpl Defect by Overexpression of PrP Transgene

The rescue of Ngsk $Prnp^{0/0}$ mice by high level expression of a MoPrP-A encoded by a transgene array argues that Dpl overexpression in these mice can be overcome by high levels of $PrP^C$ (Nishida et al, in press). In these Tg(P)Ngsk/$Prnp^{0/0}$ mice that were rescued by overexpression of a wild type MoPrP-A, the transgene was constructed using the Syrian hamster Cos.Tet vector, which does not contain the Dpl ORF (Scott et al., *Protein Sci.* 1:986–997 (1992)). The levels of PrnD MRNA in Tg(P)Ngsk/$Prnp^{0/0}$ mice did not differ from Ngsk $Prnp^{0/0}$ littermates lacking this transgene. Thus, if cerebellar degeneration is directly attributable to overexpression of PrnD, "rescue" by overexpression of PrP must proceed by a postranscriptional mechanism: presumably PrPC titrates-out the toxic effects of Dpl, perhaps by a direct physical interaction or competition for a common receptor.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated nucleic acid sequence or complement thereof comprising a nucleic acid sequence encoding a human doppel (Dpl) polypeptide (SEQ ID NO:2).

2. The isolated nucleic acid sequence of claim 1 comprising a nucleic acid sequence of SEQ ID NO:1.

3. A recombinant expression vector comprising the nucleic acid sequence of claim 2.

4. An isolated recombinant host cell containing the nucleic acid sequence of claim 2.

5. A method for identifying a nucleic acid homologous to the nucleic acid of claim 1, the method comprising the steps of:

contacting a nucleic acid probe with a test nucleic acid under stingent conditions, the probe comprising at least 15 contiguous nucleotides of a nucleic acid sequence encoding a human doppel (Dpl) polypeptide (SEQ ID NO:2); and detecting hybridization of the probe with the test nucleic acid;

wherein detection of hybridization of the probe to the test nucleic acid indicates that the nucleic acid shares sequence homology with the human Dpl polypeptide-encoding nucleic acid.

6. A method for identifying a biologically active agent that modulates human doppel (Dpl) activity, the method comprising:

combining a candidate agent with any one of:

(a) a cell comprising a nucleic acid encoding a mammalian Dpl polypeptide; or (b) a cell comprising a nucleic acid encoding a mammalian Dpl promoter sequence operably linked to a nucleic acid encoding a report gene; and determining the effect of said agent on Dpl activity.

7. The method of claim 6, wherein the nucleic acid comprises an alteration is in a Dpl promoter sequence.

8. The method of claim 6, wherein the nucleic acid comprises an alteration is in a genomic sequence encoding a Dpl polypeptide.

9. An isolated Dpl nucleic acid, wherein said nucleic acid is comprised in part of codons from a Dpl gene of a genetically diverse animal.

* * * * *

SEQUENCE LISTING

<160> NUMBER OF SEQ ID NOS: 21

<210> SEQ ID NO: 1
<211> LENGTH: 540
<212> TYPE: DNA
<213> ORGANISM: mus musculis -continued

```
<400> SEQUENCE: 1
atgaagaacc ggctgggtac atggtgggtg gccatcctct gcatgctgct tgccagccac      60
ctctccacgg tcaaggcaag gggcataaag cacaggttca agtggaaccg aaggtcctg      120 cccagcagcg gcggccagat caccgaagct cgggtagctg agaaccgccc aggagccttc     180
atcaagcaag gccggaagct ggacatcgac tttggagcag agggcaacag gtactacgcg     240
gctaactatt ggcagttccc tgatgggatc tactacgaag gctgctctga agccaacgtg     300
accaaggaga tgctggtgac cagctgcgtc aacgccaccc aggcggccaa ccaggctgag     360
ttctcccggg agaagcagga tagcaagctc caccagcgag tcctgtggcg gctgatcaaa     420
gagatctgct ccgccaagca ctgcgatttc tggctggaaa ggggagctgc gcttcgggtc     480
gccgtggacc aaccggcgat ggtctgcctg ctgggtttcg tttggttcat tgtgaagtaa     540
```

<210> SEQ ID NO: 2
<211> LENGTH: 176
<212> TYPE: PRT
<213> ORGANISM: homo sapiens

<400> SEQUENCE: 2

```
Met Arg Lys His Leu Ser Trp Trp Leu Ala Thr Val Cys Met Leu
 1               5                  10                  15

Leu Phe Ser His Leu Ser Ala Val Gln Thr Arg Gly Ile Lys His Arg
                20                  25                  30

Ile Lys Trp Asn Arg Lys Ala Leu Pro Ser Thr Ala Gln Ile Thr Glu
            35                  40                  45

Ala Gln Val Ala Glu Asn Arg Pro Gly Ala Phe Ile Lys Gln Gly Arg
        50                  55                  60

Lys Leu Asp Ile Asp Phe Gly Ala Glu Gly Asn Arg Tyr Tyr Glu Ala
65                  70                  75                  80

Asn Tyr Trp Gln Phe Pro Asp Gly Ile His Tyr Asn Gly Cys Ser Glu
                85                  90                  95

Ala Asn Val Thr Lys Glu Ala Phe Val Thr Gly Cys Ile Asn Ala Thr
                100                 105                 110

Gln Ala Ala Asn Gln Gly Glu Phe Gln Lys Pro Asp Asn Lys Leu His
            115                 120                 125

Gln Gln Val Leu Trp Arg Leu Val Gln Glu Leu Cys Ser Leu Lys His
        130                 135                 140

Cys Glu Phe Trp Leu Glu Arg Gly Ala Gly Leu Arg Val Thr Met His
145                 150                 155                 160

Gln Pro Val Leu Leu Cys Leu Leu Ala Leu Ile Trp Leu Met Val Lys
                165                 170                 175
```

<210> SEQ ID NO: 3
<211> LENGTH: 179
<212> TYPE: PRT
<213> ORGANISM: mus musculis

<400> SEQUENCE: 3

```
Met Lys Asn Arg Leu Gly Thr Trp Trp Val Ala Ile Leu Cys Met Leu
 1               5                  10                  15

Leu Ala Ser His Leu Ser Thr Val Lys Ala Arg Gly Ile Lys His Arg
                20                  25                  30

Phe Lys Trp Asn Arg Lys Val Leu Pro Ser Ser Gly Gln Ile Thr
            35                  40                  45

Glu Ala Arg Val Ala Glu Asn Arg Pro Gly Ala Phe Ile Lys Gln Gly
```

```
              50                  55                  60
Arg Lys Leu Asp Ile Asp Phe Gly Ala Glu Gly Asn Arg Tyr Tyr Ala
 65                  70                  75                  80

Ala Asn Tyr Trp Gln Phe Pro Asp Gly Ile Tyr Tyr Glu Gly Cys Ser
                 85                  90                  95

Glu Ala Asn Val Thr Lys Glu Met Leu Val Thr Ser Cys Val Asn Ala
                100                 105                 110

Thr Gln Ala Ala Asn Gln Ala Glu Phe Ser Arg Glu Lys Gln Asp Ser
                115                 120                 125

Lys Leu His Gln Arg Val Leu Trp Arg Leu Ile Lys Glu Ile Cys Ser
                130                 135                 140

Ala Lys His Cys Asp Phe Trp Leu Glu Arg Gly Ala Ala Leu Arg Val
145                 150                 155                 160

Ala Val Asp Gln Pro Ala Met Val Cys Leu Leu Gly Phe Val Trp Phe
                165                 170                 175

Ile Val Lys

<210> SEQ ID NO: 4
<211> LENGTH: 179
<212> TYPE: PRT
<213> ORGANISM: rat rattus

<400> SEQUENCE: 4

Met Lys Asn Arg Leu Gly Thr Trp Gly Leu Ala Ile Leu Cys Leu Leu
  1               5                  10                  15

Leu Ala Ser His Leu Ser Thr Val Lys Ala Arg Gly Ile Lys His Arg
                 20                  25                  30

Phe Lys Trp Asn Arg Lys Val Leu Pro Ser Ser Gly Gln Ile Thr Glu
                 35                  40                  45

Ala Gln Val Ala Glu Asn Arg Pro Gly Ala Phe Ile Lys Gln Gly Arg
 50                  55                  60

Lys Leu Asp Ile Asp Phe Gly Ala Glu Gly Asn Lys Tyr Tyr Ala Ala
 65                  70                  75                  80

Asn Tyr Trp Gln Phe Pro Asp Gly Ile Tyr Tyr Glu Gly Cys Ser Glu
                 85                  90                  95

Ala Asn Val Thr Lys Glu Val Leu Val Thr Arg Cys Val Asn Ala Thr
                100                 105                 110

Gln Ala Ala Asn Gln Ala Glu Phe Ser Arg Glu Lys Gln Asp Ser Lys
                115                 120                 125

Leu His Gln Arg Val Leu Trp Arg Leu Ile Lys Glu Ile Cys Ser Thr
                130                 135                 140

Lys His Cys Asp Phe Trp Leu Glu Arg Gly Ala Ala Leu Arg Ile Thr
145                 150                 155                 160

Val Asp Gly Leu Gln Ala Met Val Cys Leu Leu Gly Phe Ile Trp Phe
                165                 170                 175

Ile Val Lys

<210> SEQ ID NO: 5
<211> LENGTH: 19
<212> TYPE: PRT
<213> ORGANISM: Artificial Sequence
<220> FEATURE:
<223> OTHER INFORMATION: synthesized peptide

<400> SEQUENCE: 5

Asn His Cys Phe Gly Ala Glu Gly Asn Arg Tyr Tyr Ala Ala Asn Tyr
```

```
          1               5              10              15
Tyr Cys His

<210> SEQ ID NO: 6
<211> LENGTH: 23
<212> TYPE: DNA
<213> ORGANISM: homosapien

<400> SEQUENCE: 6
cggttggtcc acggcgaccc gaa                                            23

<210> SEQ ID NO: 7
<211> LENGTH: 20
<212> TYPE: DNA
<213> ORGANISM: homosapien

<400> SEQUENCE: 7
gcagatctct ttgatcagcc                                                20

<210> SEQ ID NO: 8
<211> LENGTH: 20
<212> TYPE: DNA
<213> ORGANISM: homosapien

<400> SEQUENCE: 8
cagatccacc gaagctcggg                                                20

<210> SEQ ID NO: 9
<211> LENGTH: 24
<212> TYPE: DNA
<213> ORGANISM: homosapien

<400> SEQUENCE: 9
tggtgaccag ctgcgtcaac gcca                                           24

<210> SEQ ID NO: 10
<211> LENGTH: 26
<212> TYPE: DNA
<213> ORGANISM: homosapien

<400> SEQUENCE: 10
tgggaaggcc ctgagcgaca accgtg                                         26

<210> SEQ ID NO: 11
<211> LENGTH: 28
<212> TYPE: DNA
<213> ORGANISM: Artificial Sequence
<220> FEATURE:
<223> OTHER INFORMATION: synthesized oligonucleotide

<400> SEQUENCE: 11
gctccaagct tcagaggcca cagtagca                                       28

<210> SEQ ID NO: 12
<211> LENGTH: 26
<212> TYPE: DNA
<213> ORGANISM: Artificial Sequence
<220> FEATURE:
<223> OTHER INFORMATION: synthesized oligonucleotide

<400> SEQUENCE: 12
ttacttcaca atgaaccaaa cgaaac                                         26
```

```
<210> SEQ ID NO: 13
<211> LENGTH: 19
<212> TYPE: DNA
<213> ORGANISM: Artificial Sequence
<220> FEATURE:
<223> OTHER INFORMATION: synthesized oligonucleotide

<400> SEQUENCE: 13
gagtggaggt cttcgcgca                                                   19

<210> SEQ ID NO: 14
<211> LENGTH: 40
<212> TYPE: DNA
<213> ORGANISM: Artificial Sequence
<220> FEATURE:
<223> OTHER INFORMATION: synthesized oligonucleotide

<400> SEQUENCE: 14
tcaaaactga accatttcaa cccaactgaa gtattctgcc                            40

<210> SEQ ID NO: 15
<211> LENGTH: 29
<212> TYPE: DNA
<213> ORGANISM: Artificial Sequence
<220> FEATURE:
<223> OTHER INFORMATION: synthesized oligonucleotide

<400> SEQUENCE: 15
acccagcgtt ctggcccggt attaggatt                                        29

<210> SEQ ID NO: 16
<211> LENGTH: 28
<212> TYPE: DNA
<213> ORGANISM: Artificial Sequence
<220> FEATURE:
<223> OTHER INFORMATION: synthesized oligonucleotide

<400> SEQUENCE: 16
ccagccggtt cttcatggtg aatctcgg                                         28

<210> SEQ ID NO: 17
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 17
catggtgaat ctcggttctc                                                  20

<210> SEQ ID NO: 18
<211> LENGTH: 13
<212> TYPE: DNA
<213> ORGANISM: Artificial Sequence
<220> FEATURE:
<223> OTHER INFORMATION: consensus sequence

<400> SEQUENCE: 18
gccgccacca tgg                                                         13

<210> SEQ ID NO: 19
<211> LENGTH: 13
<212> TYPE: DNA
<213> ORGANISM: Artificial Sequence
<220> FEATURE:
<223> OTHER INFORMATION: consensus sequence
```

```
<400> SEQUENCE: 19
gccgccgcca tgg                                                              13

<210> SEQ ID NO: 20
<211> LENGTH: 13
<212> TYPE: DNA
<213> ORGANISM: Artificial Sequence
<220> FEATURE:
<223> OTHER INFORMATION: match to consensus

<400> SEQUENCE: 20
agattcacca tga                                                              13

<210> SEQ ID NO: 21
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 21
atgaagaacc ggctgggtac                                                       20
```